US011564566B2

(12) United States Patent
Sayar

(10) Patent No.: US 11,564,566 B2
(45) Date of Patent: Jan. 31, 2023

(54) SYSTEM AND METHOD FOR MONITORING PUPILLARY LIGHT RESPONSE

(71) Applicant: Mordechay Sayar, Tel Aviv (IL)

(72) Inventor: Mordechay Sayar, Tel Aviv (IL)

(*) Notice: Subject to any disclaimer, the term of this patent is extended or adjusted under 35 U.S.C. 154(b) by 0 days.

(21) Appl. No.: 17/619,015

(22) PCT Filed: Jun. 26, 2019

(86) PCT No.: PCT/IL2019/050712
§ 371 (c)(1),
(2) Date: Dec. 14, 2021

(87) PCT Pub. No.: WO2020/003315
PCT Pub. Date: Jan. 2, 2020

(65) Prior Publication Data
US 2022/0296097 A1    Sep. 22, 2022

Related U.S. Application Data

(60) Provisional application No. 62/691,103, filed on Jun. 28, 2018.

(51) Int. Cl.
A61B 3/11    (2006.01)
A61B 3/00    (2006.01)
(Continued)

(52) U.S. Cl.
CPC ............ *A61B 3/112* (2013.01); *A61B 3/0008* (2013.01); *A61B 3/0025* (2013.01);
(Continued)

(58) Field of Classification Search
CPC ..... A61B 3/112; A61B 3/0008; A61B 3/0025; A61B 3/0033; A61B 3/0058; A61B 3/14; A61B 3/165
(Continued)

(56) References Cited

U.S. PATENT DOCUMENTS 7,810,928 B2   10/2010  Kandel et al.
7,854,511 B2   12/2010  Molnar et al.
(Continued)

OTHER PUBLICATIONS

Adhikari, P., et al. 2015 "The Post-Illumination Pupil Response (PIPR)", Investigative Ophthalmology & Visual Science, 56(6): 3838-3849. doi:10.1167/iovs.14-16233.
(Continued)

*Primary Examiner* — Mohammed A Hasan
(74) *Attorney, Agent, or Firm* — The Roy Gross Law Firm, LLC; Roy Gross

(57) ABSTRACT

System, devices and methods for monitoring pupillary response(s) are presented; the system comprises a light-blocking enclosure for receiving a first eye and a second eye of an individual, a light source for emitting visible light inside the enclosure and illuminating said first eye and/or second eye according to a predetermined illumination schedule, an image capturing unit for receiving visible light reflected from the first eye and/or the second eye while each eye being illuminated by said light source, and for capturing a plurality of images at a specific rate of the first eye and/or the second eye, a control unit for controlling operation of the light source and the image capturing unit and for receiving first data indicative of the plurality of images, a processing unit for processing the first data to determine second data indicative of size of pupil(s) of the first and/or second eye(s) in each of said plurality of images and processing the second data to enable determining an ophthalmological condition of the individual and generating an output signal indicative thereof, and an output interface for receiving the output signal from the control unit and presenting the output to the individual.

15 Claims, 13 Drawing Sheets

(51) Int. Cl.
*A61B 3/14* (2006.01)
*A61B 3/16* (2006.01)

(52) U.S. Cl.
CPC .......... *A61B 3/0033* (2013.01); *A61B 3/0058* (2013.01); *A61B 3/14* (2013.01); *A61B 3/165* (2013.01)

(58) Field of Classification Search
USPC ........................................................ 351/206
See application file for complete search history.

(56) References Cited

U.S. PATENT DOCUMENTS

| | | | |
|---|---|---|---|
| 2002/0024633 A1* | 2/2002 | Kim ...................... | A61B 3/112 |
| | | | 382/117 |
| 2007/0171363 A1* | 7/2007 | Chen ...................... | A61B 3/156 |
| | | | 351/200 |
| 2008/0198330 A1* | 8/2008 | Taylor .................... | A61B 3/112 |
| | | | 351/221 |
| 2011/0077548 A1* | 3/2011 | Torch ..................... | A61B 5/165 |
| | | | 600/558 |
| 2011/0170064 A1 | 7/2011 | Taylor | |
| 2016/0262611 A1 | 9/2016 | Rotenstreich | |
| 2017/0311799 A1 | 11/2017 | Holt et al. | |
| 2017/0347878 A1* | 12/2017 | Milea ...................... | A61B 3/14 |
| 2020/0214559 A1* | 7/2020 | Krueger ................. | A61B 5/163 |

OTHER PUBLICATIONS

PCT International Search Report for International Application No. PCT/IL2019/050712, dated Sep. 23, 2019, 2pp.

* cited by examiner

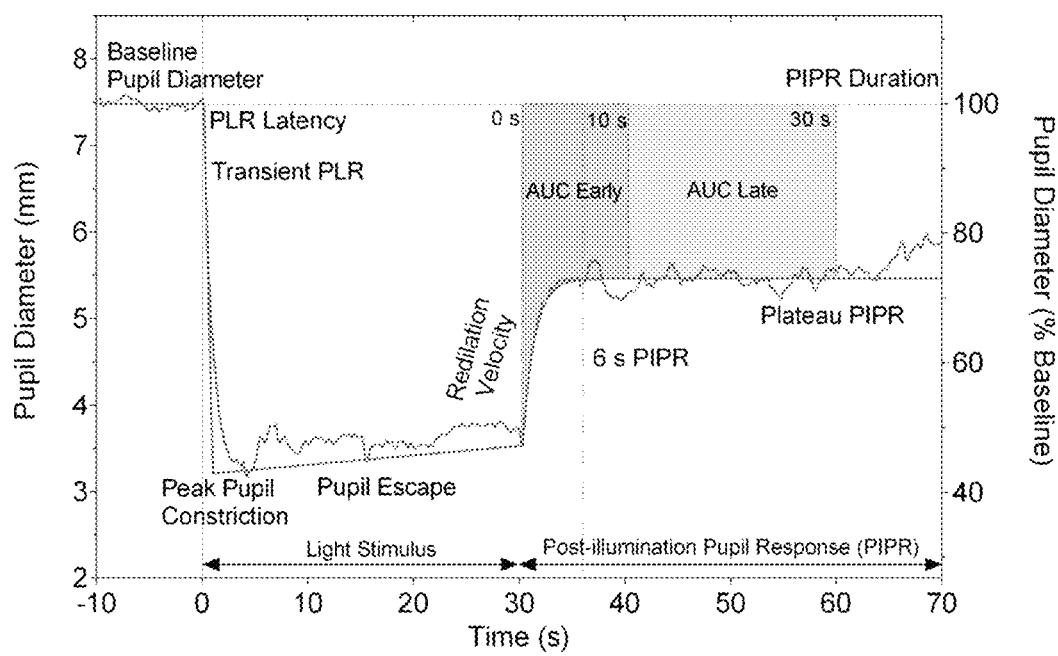
Fig. 1 (General Art)
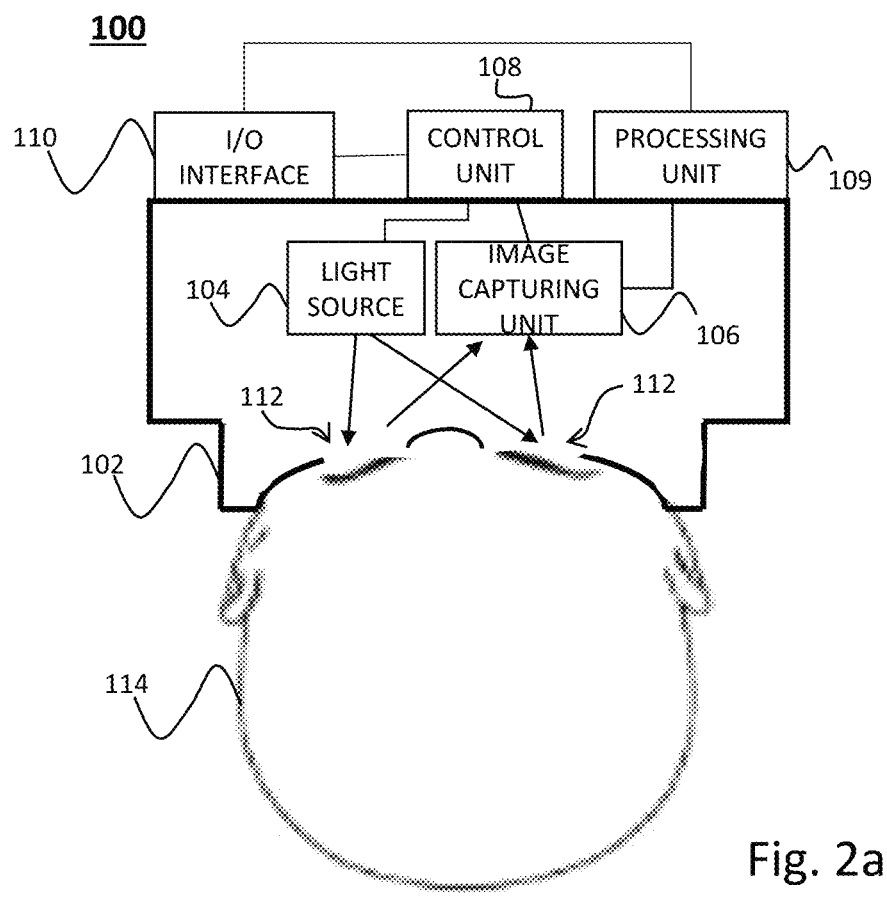
Fig. 2a

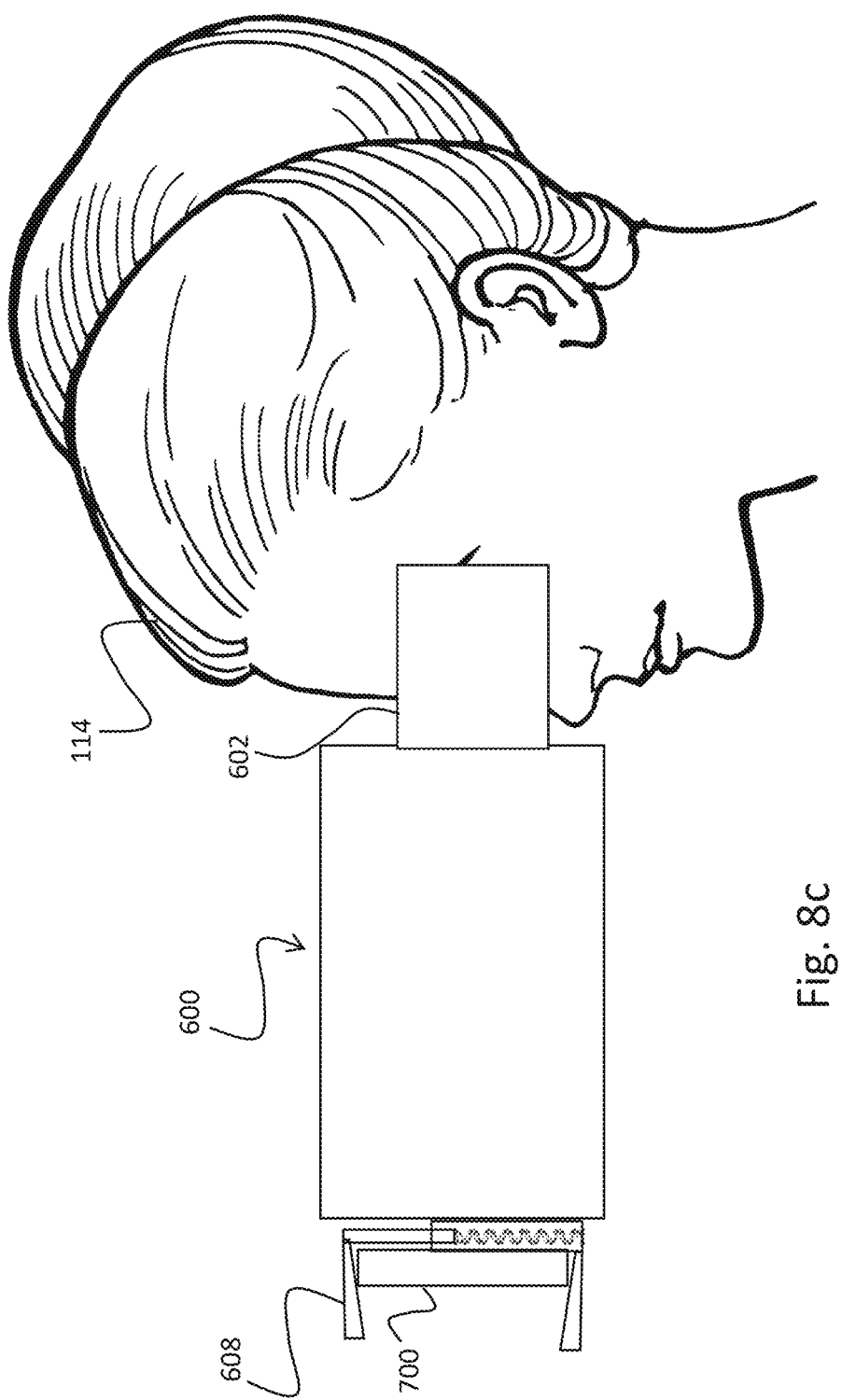

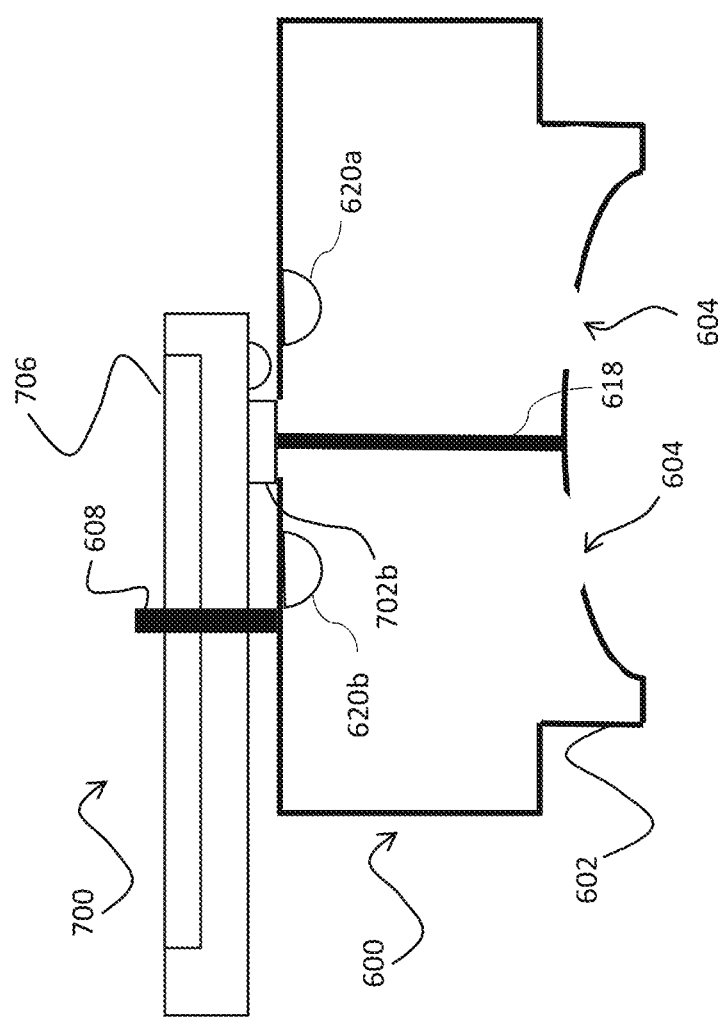

SYSTEM AND METHOD FOR MONITORING PUPILLARY LIGHT RESPONSE

CROSS REFERENCE TO RELATED APPLICATIONS

This application is a National Phase of PCT Patent Application No. PCT/IL2019/050712 having International filing date of Jun. 26, 2019, the content of which are incorporated herein by reference in its entirety.

TECHNOLOGICAL FIELD

The present invention relates generally to the field of ophthalmology, and more particularly to techniques for screening for ophthalmologic disorders and/or diseases.

BACKGROUND

Intraocular pressure (IOP) is the innate fluid pressure within the eye. IOP is maintained by the trabecular meshwork, which manages the leakage of the aqueous humor in the anterior chamber of the eye. The typical IOP of humans ranges from 7-21 mmHg with a mean of approximately 16 mmHg. Elevated IOP is an important risk factor for glaucoma, a progressive optic neuropathy that can lead to visual field defects or eventual blindness. A study carried out by Quigley and Broman in 2006 [1] predicts that the global population affected by glaucoma will reach 80 million by 2020; it further postulates that half of the people living with glaucoma are unaware that they have the disease, which can largely be attributed to a lack of resources or incentive for IOP assessment. Glaucoma also imposes a significant burden on the US healthcare system, costing roughly $3 billion USD and over 10 million visits to physicians per year Glaucoma is a group of eye diseases which result in damage to the optic nerve and vision loss. Vision loss from glaucoma, once it has occurred, is permanent. One of the main risk factors for glaucoma is increased intraocular pressure (IOP). For eye pressures a value of greater than 21 mmHg or 2.8 kPa is often used with higher pressures leading to a greater risk. Glaucoma occurs more commonly among older people and is the second-leading cause of blindness after cataracts. If treated early, it is possible to slow or stop the progression of disease with medication, laser treatment, or surgery. The goal of these treatments is to decrease IOP. IOP measurements that indicate the risk of glaucoma are generally performed by medical professionals using dedicated medical devices. Such measurements are generally not very frequent and do not account for circadian changes in IOP. Therefore, comparisons between two IOP measurements that are far apart in time and conducted at different hours of the day for the same individual may cause physicians to inaccurately diagnose the risk of glaucoma.

Relative afferent pupillary defect (RAPD) or Marcus Gunn pupil is a medical condition in which the individual's pupils constrict less, therefore appear to dilate, when a bright light is swung from an unaffected eye to an affected eye. The affected eye still senses the light and produces pupillary sphincter constriction to some degree, albeit reduced. One of the common causes of Marcus Gunn pupil is a lesion of the optic nerve (between the retina and the optic chiasm) or severe retinal disease. A second common cause of Marcus Gunn pupil is a contralateral optic tract lesion, due to the different contributions of the intact nasal and temporal hemi-fields.

Ophthalmologic biomarkers are measurable ocular features that can be used to detect and assess various pathological and non-pathological conditions affecting a subject. Non-limiting examples of ophthalmologic biomarkers include pupillary responsiveness (pupil size, pupillary light reflex, pupil motility/kinetics, etc.). Due to the usefulness of ophthalmologic biomarkers in identifying conditions of interest, various devices and techniques exist for monitoring pupil size and responsiveness characteristics. These systems are generally referred to as pupilometry systems or pupilometers. Pupillary size and responsiveness have long been a critical component in clinical assessment of subjects with neurological and physiological conditions including optic nerve disorders such as glaucoma.

U.S. Pat. No. 7,854,511 to Molnar et al. describes a portable, non-invasive binocular scanning apparatus for rapid assessment of neurological function in cases of potential trauma, disease, and/or exposure to chemical treat agents. The scanning apparatus may utilize a combination of light sources for the measurement and assessment of pupillary response, retinal imagery, and/or other ophthalmologic biomarkers. The scanning apparatus can detect and assess a wide range of neurological and physiological conditions by obtaining pertinent measurements from the retina and pupil in real time.

GENERAL DESCRIPTION

The present invention provides techniques for monitoring of the pupillary response that can be used for screening of Intraocular pressure (IOP) in one or both eyes and/or for screening of the risk of various ophthalmologic disorders and/or diseases, such as glaucoma and relative afferent pupillary defect (RAPD). The present invention provides an accessible, easy, for home-use, techniques, devices and methods, for the monitoring of the various ophthalmologic disorders/diseases. Further, the present invention utilizes, in one main aspect, visible light to both stimulate and image the pupillary response, while saving in costly and complex instrumentation.

The technique(s) of the present invention is(are) based, inter alia, on the pupillary latency that occurs when the eye is exposed to visible light. The pupillary latency, according to the present invention, means that there is a time delay in constriction of the pupil after it has been exposed to visible light. In other words, pupillary latency is the delay period between the time point at which the eye is exposed to light and the time point at which the pupil starts to constrict.

The present invention utilizes the pupillary latency effect in order to determine the size of each pupil at the end of darkness time as a reference for the pupils sizes in the images during light exposure, using only visible light. The pupil imaging is performed by capturing reflected visible light (e.g., white light or blue light or any other colored light of the visible spectrum) from the eye(s) from the onset of exposing the eye(s) to the visible light, during the pupillary latency phase and thereafter during the pupillary constriction phase. The reflected visible light is the same visible light that is used for illuminating the eyes and causing reaction thereof. In other words, the pupil is illuminated and imaged concurrently, during illuminating the pupil by the same visible light source. This enables determining the pupil full and/or relative size(s) before it starts to constrict and during the constriction. In contrast, in U.S. Pat. No. 7,854,511 two light sources are used: a first source of visible light for causing eyes' reaction and a second source of IR radiation for continuous imaging.

By using a visible light source, the invention can advantageously utilize a smartphone device as the imaging means, i.e. the device's camera, and possibly, in some embodiments, as the source for the illuminating visible light (for example, via the flash light in the device). Together with a specifically built apparatus, the smartphone device and the apparatus form a portable, easy to use, pupilometer. Additionally, a specifically built mobile application that can be downloaded and run on the smartphone device, provides a tool for processing and analysis of the obtained data (image data) to thereby determine the pupillary response that is indicative of various ophthalmological conditions.

Moreover, as shown in FIG. 1 (from Prakash Adhikari; Andrew J. Zele; Beatrix Feigl, "The Post-Illumination Pupil Response (PIPR)", Investigative Ophthalmology & Visual Science June 2015, Vol. 56, 3838-3849. doi:10.1167/iovs.14-16233), the general art indicates that after being exposed to darkness, for a first predetermined period of time, the pupil of an eye reaches a certain maximal size. When the pupil is exposed to light, for a predetermined second time period, the pupil constricts and reaches a minimal size. When the pupil is then exposed to darkness, for a third predetermined period of time (typically shorter than the first period), the pupil dilates up to a second size that is greater than the minimal size and smaller than the maximal size. These changes in the pupil size can be indicative of a condition of the eye.

Some of the techniques of the present invention are based on the following. It is very rare that glaucoma appears in both eyes at the same time; As mentioned above elevated IOP is an important risk factor for glaucoma, a progressive optic neuropathy that can lead to visual field defects or eventual blindness. IOP affects the reaction of the pupil to light; and the same pupil may react differently to light under different conditions. Accordingly, analysis of the simultaneous reaction of both pupils to light can give an indication on whether an individual is at risk for glaucoma. The inventor has found that if the changes in the both pupils sizes of the individual differ from each other by a certain extent, typically as a result of different IOPs of the two eyes, this difference may be indicative of glaucoma condition/risk.

Therefore, some embodiments of the present invention relate to a technique for operating a light emitting unit to emit visible light illuminating both eyes/pupils concurrently, according to a schedule that allows measurement of the size of both pupils during the latency period and following the latency period. In this manner, the measured sizes of the pupils allow extraction of at least one feature of the size variance of each pupil.

A comparison between the feature of the first pupil and the corresponding feature of the second pupil can be performed. If the discrepancy between the feature of the first pupil and the corresponding feature of the second pupil is larger than a certain threshold, this may indicate that IOPs of the two eyes differ from each other, a fact that may indicate a risk for glaucoma.

Some other techniques of the present invention, utilizing the pupillary latency principle, are directed towards assessment of RAPD condition. Also here, the pupil(s) is(are) imaged while being illuminated with visible light based on the known swinging-flashlight test principles, as will be detailed further below.

Thus, according to one broad aspect of the present invention, there is provided a pupillary response monitoring system comprising:

(a) a light-blocking enclosure with an open end for receiving a first eye and a second eye of an individual;

(b) a light source, configured and operable for emitting visible light inside the enclosure and illuminating said first eye and/or second eye, according to a predetermined illumination schedule;

(c) an image capturing unit, configured and operable for receiving visible light reflected from the first eye and/or the second eye, while each eye being illuminated by said light source, and for capturing a plurality of images, at a specific rate, of the first eye and/or the second eye;

(d) a control unit configured and operable for:
controlling an operation and the illumination schedule of the light source;
controlling an operation of the image capturing unit; and
receiving from the image capturing unit first data indicative of the plurality of images;

(e) a processing unit configured and operable for:
processing the first data to determine second data indicative of a size of a pupil of the first eye and/or a size of a pupil of the second eye in each of said plurality of images;
processing the second data to enable determining an ophthalmological condition of the individual using the system; and
generating an output signal indicative of said ophthalmological condition; and (f) an output interface, configured for receiving the output signal from the processing unit and presenting the output to the individual.

In some embodiments, the processing unit is remote and being configured and operable to communicate with said control unit, to receive said plurality of images, via network.

In some embodiments, the control unit is configured and operable to control the image capturing unit to capture the plurality of images at the specific rate such that at least one image is captured for the illuminated first and/or second eye during 0.3 seconds of onset of the illumination schedule.

In some embodiments, the control unit is configured and operable to control the operation of the light source to define a required exposure and illuminate the first and second eyes simultaneously, and to control the operation of the image capturing unit to determine and lock focus thereof and to capture the plurality of images of the first and second eyes simultaneously, and said processing unit is configured and operable to process said second data by extracting from the second data at least one feature indicative of a variance of the size of the pupil of the first eye and the size of the pupil of the second eye, and performing a comparison of the at least one feature between the pupils; and upon determining a difference higher than a threshold between the sizes of the pupils, generating said output signal indicative of the ophthalmological condition. The control unit may be configured and operable to control said predetermined illumination schedule comprising: (i) a first illumination step comprising exposing the first and second eyes to darkness for a first time period; (ii) a second illumination step comprising illuminating the first and second eyes for a second time period and capturing images of the first and second eyes simultaneously; (iii) a third illumination step comprising exposing the first and second eyes to darkness for a third time period shorter than the first time period; (iv) a fourth illumination step comprising illuminating the first and second eyes for a fourth time period and capturing images of the first and second eyes simultaneously. In such case, the ophthalmological condition may be a difference in intra ocular pressure (IOP) between the first and second eyes.

In some embodiments, the control unit is configured and operable to control the operation of the light source to define a required exposure and illuminate one eye, and to control the operation of the image capturing unit to determine and lock focus thereof and to capture the plurality of images of the eye, and said processing unit is configured and operable to process said second data by extracting from the second data at least one feature indicative of a variance of the size of the pupil of the eye, and generating said output signal indicative of the ophthalmological condition. The control unit may be configured and operable to control said predetermined illumination schedule comprising: (i) a first illumination step comprising exposing the eye to darkness for a first time period; (ii) a second illumination step comprising illuminating the eye for a second time period and capturing images of the eye; (iii) a third illumination step comprising exposing the eye to darkness for a third time period shorter than the first time period; (iv) a fourth illumination step comprising illuminating the eye for a fourth time period and capturing images of the eye. In such case, the ophthalmological condition may be a value of intra ocular pressure (IOP) in said eye. The processing unit may be configured and operable to generate said value of IOP by comparing said at least one feature indicative of a variance of the size of the pupil of the eye to a database.

In some embodiments, the control unit is configured and operable to control the operation of the light source to define a required exposure and illuminate the first and second eyes sequentially, and to control the operation of the image capturing unit to determine and lock focus thereof and to capture the plurality of images of each of the first and second eyes while being illuminated, and said processing unit is configured and operable to to process said second data to determine, for each eye, third data indicative of a size of the pupil of each eye at least at a beginning of an illumination session and at an end of the illumination session, and to perform a comparison of the sizes of each pupil, and upon determining an increase in the size of the same pupil during the illumination session, generate said output signal indicative of the ophthalmological condition. The control unit may be configured and operable to control said predetermined illumination schedule comprising: (i) a first illumination step comprising exposing the first and second eyes to darkness for a first time period; (ii) a second illumination step comprising illuminating the first eye for a second time period and capturing images of the first eye; (iii) a third illumination step comprising illuminating the second eye for a third time period and capturing images of the second eye; (iv) a fourth illumination step comprising illuminating the first eye for a fourth time period and capturing images of the first eye. The predetermined illumination schedule may further comprise: (v) a fifth illumination step comprising illuminating the second eye for a fifth time period and capturing images of the second eye. In such case, the ophthalmological condition is Relative Afferent Pupillary Defect (RAPD).

In some embodiments, the light source comprises a plurality of light emitting units. In some embodiments, a first part of said light emitting units may be configured for illuminating said first eye and a second part of said light emitting units may be configured for illuminating said second eye.

In some embodiments, the light-blocking enclosure comprises a light directing arrangement configured and operable to direct light from said light source to said first and/or second eye(s).

In some embodiments, the system further comprises a mobile device, wherein said mobile device comprises said image capturing unit, said control unit and said output interface. The mobile device may further comprise said light source. The mobile device may be a smartphone or a tablet.

According to another broad aspect of the present invention, there is provided a device for use in monitoring pupillary response, the device being configured for mounting on an individual's face, the device comprising a light blocking enclosure configured for blocking light from outside the enclosure to reach a first and a second eye of the individual, said enclosure comprising:

(a) a first opening for receiving said first and second eyes;
(b) a second opening;
(c) a smartphone holder located on an outer side of the enclosure in a vicinity of the second opening and configured for engaging with a smartphone such that a back side of the smartphone covers the second opening and such that at least an aperture of a camera of the smartphone is located at the second opening and has a line of sight to the first opening via the second opening.

According to yet another broad aspect of the present invention, there is provided a device for use in monitoring pupillary response, the device being configured for mounting on an individual's face, the device comprising a light blocking enclosure configured for blocking light from outside the enclosure to reach a first and a second eye of the individual, said enclosure comprising:

(a) a first opening for facing the individual's face and for receiving said first and second eyes;
(b) a light source comprising one or more visible light emitting units having line(s) of sight with said first and/or second eye(s);
(c) a second opening;
(d) a smartphone holder located on an outer side of the enclosure in a vicinity of the second opening and configured for engaging with a smartphone such that a back side of the smartphone covers the second opening and such that an aperture of a camera of the smartphone is located at the second opening and has a line of sight to the first opening via the second opening; and
(e) a communication unit configured and operable to enable controlling said light source by a smartphone when the smartphone is engaged with the enclosure.

According to yet another broad aspect of the present invention, there is provided a method for monitoring pupillary response, the method comprising illuminating a first and/or a second eye of an individual with visible light according to a predetermined illumination schedule and capturing a plurality of images, at a specific rate, of said first and/or second eye(s) by detecting reflected light of said visible light, and processing said images to determine for each image a pupil parameter indicative of a size of a pupil of said first and/or second eye(s), and analyzing said pupil parameter in the plurality of images to thereby determine an ophthalmological condition of the individual.

In some embodiments, the first and second eyes are illuminated simultaneously, and said analyzing of the pupil parameter of the first and second eyes comprises performing a comparison of at least one feature between the pupils and upon determining a difference higher than a threshold in said at least one feature between the pupils, generating an output indicative of the ophthalmological condition. The ophthalmological condition may be a difference in intra ocular pressure (IOP) between the first and second eyes.

In some embodiments, the predetermined illumination schedule comprises: (i) a first illumination step comprising exposing one of the first and second eyes to darkness for a first time period; (ii) a second illumination step comprising illuminating the same eye for a second time period and capturing images of the eye; (iii) a third illumination step comprising exposing the eye to darkness for a third time period shorter than the first time period; (iv) a fourth illumination step comprising illuminating the eye for a fourth time period and capturing images of the eye. The ophthalmological condition may be a value of intra ocular pressure (IOP) in the eye. The value of IOP may be generated by analyzing said pupil parameter and determining at least one feature indicative of a variance of the size of the pupil of the eye, and comparing said feature to a database.

In some embodiments, the first and second eyes are illuminated sequentially, and said analyzing of the pupil parameter comprises determining a size of the pupil of each eye at least at a beginning of each eye illumination and at an end of each eye illumination, and performing a comparison of the sizes of each pupil and to perform a comparison of the sizes of each pupil, and upon determining an increase in the size of the same pupil during the illumination session, generate an output indicative of the ophthalmological condition.

In some embodiments, the predetermined illumination schedule comprises: (i) a first illumination step comprising exposing the first and second eyes to darkness for a first time period; (ii) a second illumination step comprising illuminating the first eye for a second time period and capturing images of the first eye; (iii) a third illumination step comprising illuminating the second eye for a third time period and capturing images of the second eye; (iv) a fourth illumination step comprising illuminating the first eye for a fourth time period and capturing images of the first eye. In some embodiments, the predetermined illumination schedule further comprises: (v) a fifth illumination step comprising illuminating the second eye for a fifth time period and capturing images of the second eye. The ophthalmological condition may be Relative Afferent Pupillary Defect (RAPD).

According to yet another broad aspect of the present invention, there is provided a non-transitory computer readable medium including one or more sequences of instructions for monitoring pupillary response of an individual, wherein execution of the one or more sequences of instructions by one or more processors of a computing device comprising a camera causes the computing device to perform a process comprising:

activating and controlling a light source to illuminate a first and/or a second eye(s) of the individual according to a predetermined illumination schedule;

acquiring a plurality of images of said first and/or second eye by said camera, while being illuminated by said light source, according to a specific rate;

processing said plurality of images to thereby determine quantitative data indicative of a size of a first pupil of the first eye and/or a size of a second pupil of the second eye in each of said plurality of images; and analyzing said quantitative data and determining whether the quantitative data is indicative of one of the following ophthalmology conditions:

difference in Intraocular Pressure (IOP) between the first and second eyes,

Value of IOP in at least one of the first and second eyes,

Relative Afferent Pupillary Defect (RAPD); and generating corresponding output data to be presented to the individual.

In some embodiments, the one or more sequences of instructions comprise:

controlling said light source to illuminate the first and second eyes simultaneously;

acquiring said plurality of images of the first and second eyes simultaneously;

processing said quantitative data by extracting from the quantitative data at least one feature indicative of a variance of the first pupil size and the second pupil size, and performing a comparison of the at least one feature between the first and second pupils; and analyzing said comparison and upon determining a difference higher than a threshold between the first and second pupils, generating said output signal indicative of difference in Intraocular Pressure for said individual.

In some embodiments, the one or more sequences of instructions comprise:

controlling said light source to illuminate the first and second eyes sequentially;

acquiring said plurality of images of each of the first and second eyes while being illuminated;

processing said quantitative data and determining, for each eye, a size of the pupil of each eye at least at a beginning of an illumination session and at an end of the illumination session, and performing a comparison of the sizes of each pupil; and analyzing said comparison and upon determining an increase in the size of the pupil of the same eye during the illumination session, generating said output signal indicative of Relative Afferent Pupillary Defect (RAPD) for said individual.

In some embodiments, the one or more sequences of instructions comprise:

controlling said light source to illuminate one of the first and second eyes;

acquiring said plurality of images of the eye while being illuminated;

processing said quantitative data by extracting from the quantitative data at least one feature indicative of a variance of the pupil size, and performing a comparison of the at least one feature to with respect to a database; and generating said output signal indicative of value of IOP in the eye.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 illustrates a general pupil response to light as a function of pupil area, e.g. diameter, against time;

FIGS. 2a-2b schematically illustrate in a block diagram an non-limiting example of a system for monitoring pupillary response according to some embodiments of the invention;

FIGS. 8a-8f illustrate exemplary non-limiting embodiments of different components of a system for monitoring pupillary response to light utilizing a smartphone.

DETAILED DESCRIPTION OF EMBODIMENTS

Figure 2B:
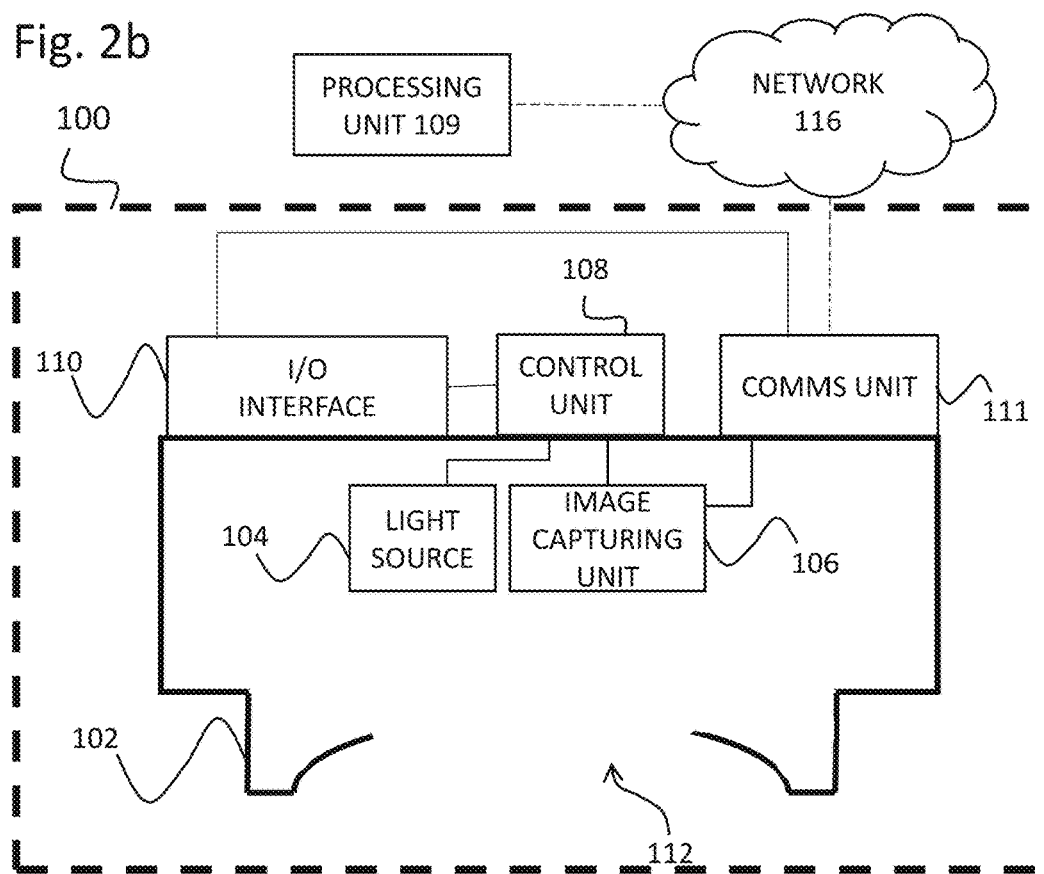

Reference is made to FIGS. 2a-2b, which are schematic drawings illustrating a non-limiting exemplary system 100 in accordance with the present invention for monitoring individual's pupil response to visible light. The system 100 may be configured as a portable self-pupilometer that can be easily used by a user or a user's caretaker, and does not need the assistance or intervention of medical personnel. The system 100 includes a light-blocking enclosure 102, a light source 104, an image capturing unit 106, a control unit 108, a processing unit 109, and an input/output (I/O) interface 110.

In some embodiments, the system 100 may be formed in a single apparatus that includes all of the above-mentioned utilities/parts/units. In some other embodiments, the system 100 may be distributed between two or more separate apparatuses/devices, as will be further described below. In one specific non-limiting example, as will be described further below, the system includes the light-blocking enclosure being in a first housing and the light source, the image capturing unit, the control unit, the processing unit and the I/O interface being in a second housing, such as in a smartphone.

The light blocking enclosure 102 has an open end 112 for receiving a first eye and a second eye of an individual 114. In some embodiments of the present invention, the open end 112 is divided into two discrete openings, each configured for receiving a respective eye, as shown in FIG. 2a. In some other embodiments, the open end 112 is a continuous, single, opening and configured for receiving both eyes together, as shown in FIG. 2b. When the enclosure 102 receives the individual's eyes, light from outside the enclosure is prevented from reaching the individual's eyes.

As described above, the light source 104 may be located inside the enclosure 102, or in a separate housing, and is configured for emitting visible light according to a desired schedule in order to stimulate the individual's eyes. The light source may be configured for emitting light waves having a certain wavelength range or discrete light wave ranges. The light source may include one or more light emitting units, such as a white light-emitting diodes (LEDs) or a colored (e.g., blue LEDs) or a white LED covered by a colored (e.g., blue) filter (for example, yielding Blue light having a wavelength of 450-500 nm). In case the light source 104 includes more than one light emitting unit, those can be operated collectively or individually. For example, all the light emitting units are operated concurrently to produce a single light beam being directed to one or both eyes. In another example, each eye has its dedicated exciting light emitting unit(s), this can help in reducing cross-talk between the light directed to the two eyes. More specifically, in some embodiments of the invention, only one eye at a time should be illuminated while the other eye should be kept in darkness; accordingly, the light blocking enclosure can be configured with a barrier (see FIG. 8f below) between the eyes forming two separate compartments each dedicated for receiving one eye and a light source (one or more lighting elements) configured to illuminate the eye in the same compartment. Further, the barrier can be removable, such that the same light blocking enclosure can be configured for illuminating the eyes separately or collectively as the case may be and as will be described further below.

The image capturing unit 106 is configured for receiving light emitted by the light source 104 and reflected from the eyes, in order to capture a plurality of images of the first eye and the second eye, at a desired rate (which may be, for example, 10, 15 or 20 images/sec.). In some embodiments, the image capturing unit 106 is configured for capturing simultaneous images of both eyes. The image capturing unit 106 may include a single device configured for capturing images of both eyes or two devices, each configured for capturing images of a respective eye. The image capturing unit may be located inside the enclosure or attached to the enclosure and is configured for having a line of sight with the eyes. The image capturing unit is also configured for being focused on the eyes when the eyes are received by the eye-receiving open end, in order to yield focused images of the individual's pupils.

The image capturing unit 106 may include optical elements and a sensor (not shown). The optical elements may include refractive and/or diffractive and/or reflective elements configured for directing light reflected from the eyes to the sensor. The sensor is configured for receiving the light directed by the optical elements and yielding image data therefrom. The sensor may, for example, include a photosensitive charge-coupled device (CCD).

The input/output interface 110 is configured and operable for receiving an input from the user or user's caretaker, e.g. an input for starting a measurement session and for transmitting an input signal indicative of the input to the control unit 108. The input/output interface 110 is further configured and operable for receiving an output signal from the control unit 108 and/or the processing unit 109, and for yielding an output associated with the output signal to the user or the user's caretaker, as will be further explained below.

The control unit 108 is configured for controlling the operation of the light source 104 and of the image capturing unit 106, to turn the light source (or its individual light emitting elements on an individual or collective basis) on and off according to a desired schedule and to cause the image capturing unit to capture images at least when the light source is on. For this purpose, the control unit 108 may include a memory utility to store instructions and a processor utility to execute those instructions.

The input/output interface 110 is configured for receiving an input from the user or the user's caretaker when the user's eyes are received by the enclosure. The input/output interface 110 may include an input unit, such as a button, a touch screen, or an audio instruction unit (configured for receiving audio instructions from the user), the input unit being configured for receiving an input from the user when the user is ready to start the measurement session. When such input from the user is received, the control unit 108 starts the measurement session by activating the light source 104 and the image capturing unit 106, according to a predetermined schedule.

In some embodiments of the present invention, when a user uses the system 100 for the first time, a profile of the user is created in the control unit's memory utility. The profile may include an identifier of the user, such as a name, a number, or a picture.

Each time the user uses the system 100, the control unit 108 operates the light source 104 and the image capturing unit 106 to respectively adjust their optimal exposure and focus on the eyes of the user.

The system 100 may communicate with a processing unit 109, which can be internal or external to the system 100. The processing unit 109 is configured for receiving image data from the image capturing unit 106 and for processing the image data in order to compare the behavior of the first eye's pupil (first pupil) with the behavior of the second eye's pupil (second pupil). For this purpose, the processing unit 109 includes a memory utility configured to store instructions and a processor utility to execute those instructions. The memory utility and the processor utility used by the control unit 108 and the processing unit 109 may be the same or may be different.

In some embodiments of the present invention, the processing unit 109 can be an integral part of the control unit 108. In some embodiments, the processing unit 109 is local and physically joined to the enclosure, as shown in FIG. 2a. In this case, the processing unit 109 is part of the system 100. In other embodiments of the present invention, the processing unit 109 is remote, e.g. residing in the cloud or accessible via the internet, and is reachable via a communication unit 111, for example via a network 116, as shown in FIG. 2b. In some embodiments, a single remote processing unit 109 may serve a plurality of the systems 100.

The processing unit 109 receives from the image capturing unit 106 first data (image data) indicative of a plurality of images of the eyes. The communication between the processing unit 109 and the image capturing unit 104 may be direct (wired or wireless) as shown in FIG. 2a, or may be mediated by the communication unit 111, as shown in FIG. 2b. The processing unit 109 is configured for processing the first data (image data) in order to determine second data indicative of a size of the first pupil and a size of the second pupil at different time points for each pupil. In some embodiments, the processing by the processing unit 109 includes extracting from the second data at least one feature of a variance of the first pupil size and at least one corresponding feature of a variance of the second pupil size; performing a comparison of the feature between the first and second eyes; and generating a signal according to a result of the comparison. In some other embodiments, the processing by the processing unit 109 includes comparing the sizes of the same pupil and/or both pupils at different time points during the measurement session. In some other embodiments, the processing by the processing unit 109 includes calculating speed of constriction of the pupil(s) by utilizing the change in the pupil(s) change as a function of time.

In one specific example, when the system 100 is used to diagnose risk for Glaucoma, by detecting IOP difference between both eyes, the processing unit 109 is configured to compare the sizes of first and second pupils at specific time points during the measurement session, and upon detecting that the sizes of the first and second pupils differ by a certain threshold, this could indicate that an IOP difference exists between both eyes which means a risk for Glaucoma.

Since it is known that generally glaucoma does not affect both eyes simultaneously, and because elevated IOP is known to affect pupil behavior, one explanation for the difference in the pupil behavior may be elevated IOP in one of the eyes. Therefore, if the difference in the feature values between the first and second pupils is larger than a certain threshold, or if the ratio between the feature values differs from 1 in accordance with a predetermined threshold, the individual may be at risk for glaucoma.

Therefore, if the difference between the behaviors of the pupils is over a certain threshold, the processing unit 109 is configured for generating an output signal indicative of this fact.

In another specific example, as will be described further below, the system can be used in diagnosing risk for relative afferent pupillary defect (RAPD). In this particular case, the processing of the images for both eyes includes determining sizes of the pupils in the different images and comparing the sizes according to a predetermined algorithm to thereby generate an output signal indicative of the risk for RAPD.

The output signal is received by the I/O interface 110 (either directly from the processing unit 109 as shown in FIG. 2a, or from the processing unit 109 via the communication unit 111 as shown in FIG. 2b) and causes the I/O interface 110 to generate an output that advises the individual to consult with medical personnel. If, on the other hand, the difference between the behaviors of the pupils is below the threshold in the case of risk for Glaucoma test, or no risk for RAPD is detected, the processing unit 109 is configured for generating an output signal indicative of this fact, e.g. the output signal may cause the I/O interface to generate an output that advises the individual that there is no need to consult with medical personnel about elevated IOP or RAPD.

As mentioned above, a person's IOP may change depending on the time of the day or physical activity. Therefore, in some embodiments of the present invention, the processing unit 109 is configured for storing the results of a plurality of tests repeated over a few days, and for processing the results of the plurality of tests in order to determine whether the user has elevated IOP in one or both eyes.

The input/output interface 110 may include any output device configured for receiving the signal from the control unit 108 and generating an output according to the signal. Therefore, the output interface is configured for relaying a message to a user. The output interface 110 may include one or more of a screen, a light source, a speaker, and a haptic device.

In some embodiments of the present invention, the input/output interface 110 is configured for warning the user to keep eyes open (i.e. not to blink and to look forward) for a certain time interval before the light source is turned on and the image capturing unit captures images. Optionally, the output interface is configured for emitting soothing sounds (e.g., soothing music or natural sounds, such as the sounds of sea waves) to soothe the user. In this manner, the assessment of the eyes is made when the user is soothed and calm, and IOP is less affected by possible stress/emotion of the user.

Figure 3:
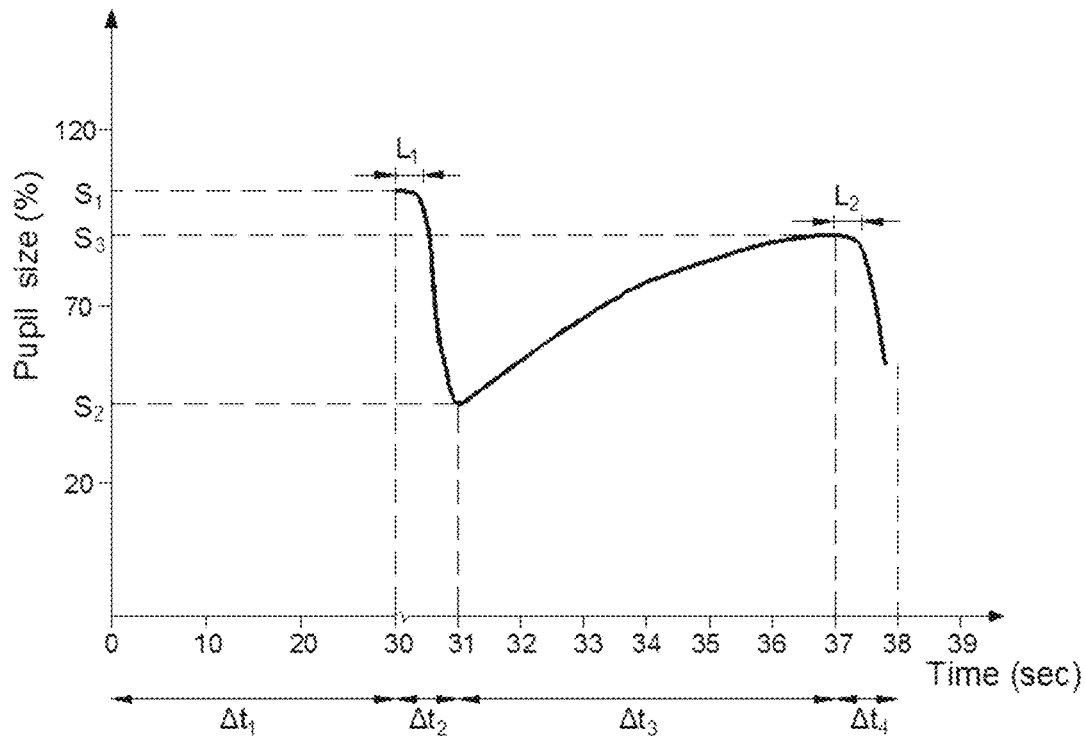
FIG. 3 illustrates a non-limiting exemplary measurement session for monitoring pupillary response, executed in accordance with some embodiments of the present invention.

Reference is now made to FIG. 3, which is a graph illustrating a measurement session for determining pupillary response, executed in accordance with the present invention, in the case of IOP difference test, or in the case of measuring absolute value of an IOP in at least one eye, or in case of detecting any other disease described herein. Measured data indicative of a time variance of a pupil's size, according to some embodiments of the present invention, are shown. The measurement session may be executed by using the system 100 of the present invention. It should be noted that in the graph a measurement session of one of the two pupils is shown. Generally, before the user puts on the light blocking enclosure, he/she types in the setup parameters and initiates the test procedure. After a predetermined delay time (not shown in the figure, to let the user put on the light blocking enclosure), the system activates the light source 104 and the image capturing unit 106 in order to determine and lock the exposure and the focus. Then, the measurement session starts as follows.

The light source 104 of system 100 is controlled (e.g., by the control unit 108) to be off for a first time period ($\Delta t_1$), in order to keep the individual's eyes in darkness and ensure that the individual's pupils dilate and achieve a first size $S_1$ (typically, a maximal size). The first time period may be, for example, 20 seconds, 30 second, 40 seconds. Following the first time period, the light source 104 is turned on for a second time period ($\Delta t_2$) to illuminate both eyes simultaneously in order to cause the pupils to constrict and achieve a second size $S_2$. During $\Delta t_2$, the image capturing unit 106 is configured to capture images of both eyes at a certain rate. Following the second time period, the light source is turned off and kept off for a third time period ($\Delta t_3$), in order to allow the pupil(s) to dilate to a third size $S_3$. Following the third time period, the light source is turned on for a fourth time period ($\Delta t_4$). During $\Delta t_4$, the image capturing unit 106 is configured to capture images of both eyes at a certain rate.

When the light source is off, the interior of the enclosure 102 is dark, and therefore images captured by the image capturing unit are dark as well, unless the image capturing unit is an infra-red imager for example. To this end, in some embodiments, the light source unit 104 and/or the image capturing unit 106 may be configured with infra-red source and/or infra-red sensor, which can be activated at least during the third time period ($\Delta t_3$) in order to also capture images of the eye(s) when not exposed to visible light. The image data collected during this period can be used as well in the analysis of the pupils behavior during the period ($\Delta t_3$) to extract relevant features indicative of eye condition.

As mentioned before, the delay period between the time point at which the eye is exposed to light and the time point at which pupils start constricting is called the pupillary latency period. During the latency period, the pupils' sizes remain as the sizes before illumination. Therefore, at the beginning of $\Delta t_2$, the light does not affect the pupil size in the first latency period $L_1$. Similarly, at the beginning of $\Delta t_4$, the light does not affect the pupil size in the second latency period $L_2$. This fact enables the image capturing unit, which is based on a visible light sensor, to capture images of the pupils during $L_1$ and $L_2$ when the pupils are dilated (and have sizes $S_1$ and $S_3$) as they were at the end of the darkness periods $\Delta t_1$ and $\Delta t_3$.

Latency periods may vary between different people, and may need to be evaluated for each test. In some embodiments of the present invention, the end of the latency period is determined by the processing unit 109, by identifying a predetermined change (reduction) in the pupil size when analyzing the captured images. Once the final data point of the latency period is evaluated, the size of the pupil during the latency period is determined by calculating median value of the measured pupil sizes at the different data points within the determined latency period.

In a non-limiting example of the present invention, a schedule is set for the light source, so that $\Delta t_1$ is about 30 seconds, $\Delta t_2$ is about 1 second, $\Delta t_3$ is about 6 seconds, and $\Delta t_4$ is about 1 second. It should be noted that the figure is not in scale (as illustrated by the broken arrow indicating $\Delta t_1$). It was shown, in Prakash Adhikari et al, mentioned above, that for short wavelength light these time values showed the least intra- and inter-individual coefficients of variation CV<0.2. Optionally, the control unit 108 is configured for storing a plurality of different schedules for the light source.

Figure 4A:
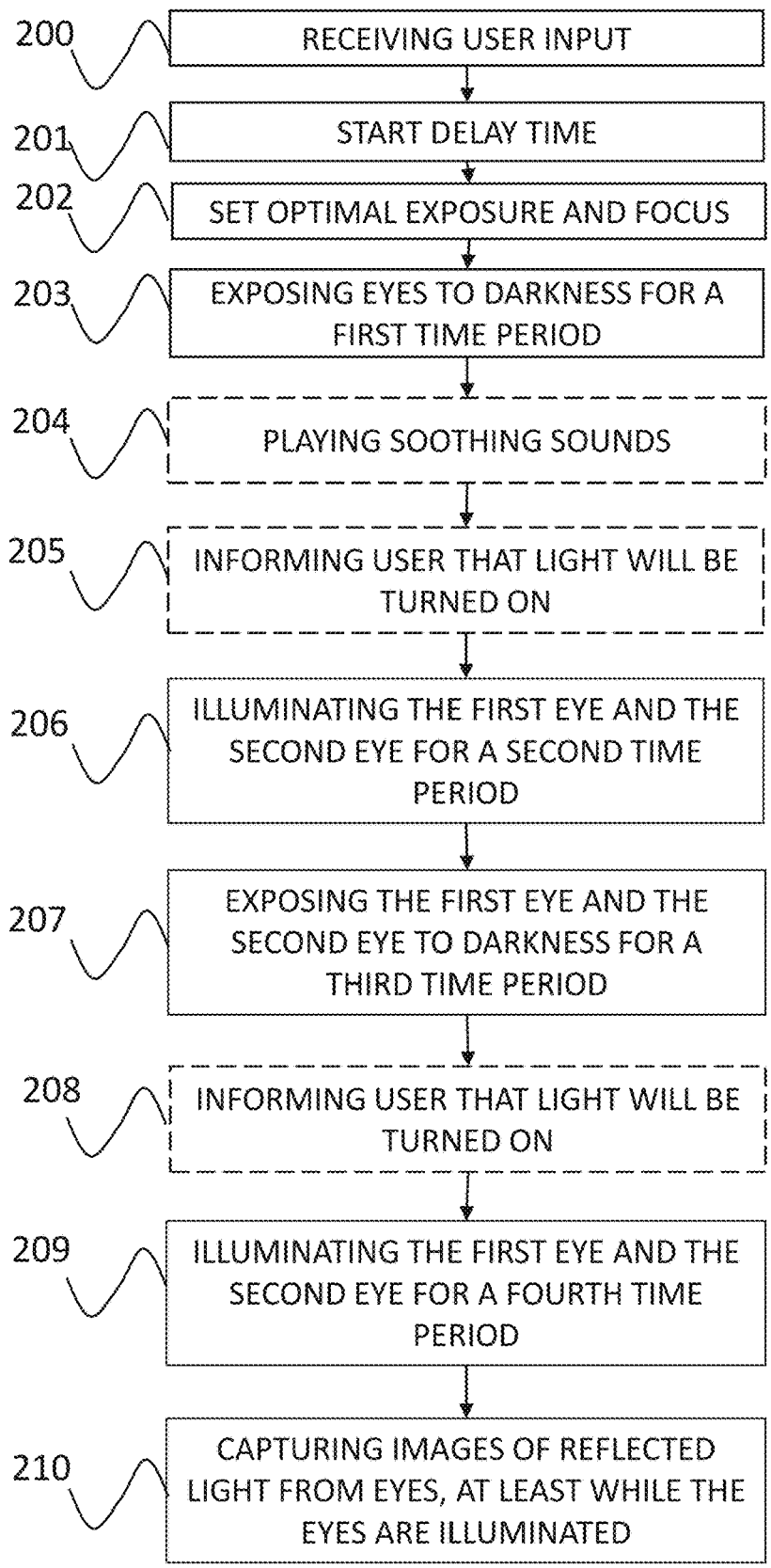
FIGS. 4a-4c illustrate non-limiting examples of methods for collecting and processing images of a person's pupils in order to determine conditions of the person's eyes.

Reference is now made to FIG. 4a, which is a flowchart 190 illustrating a non-limiting exemplary method for collecting images that can be processed to determine a condition of a person's eyes IOP. It is noted that the method 190 can be executed by using the system 100.

At 200, the user turns on the system to start the test, chooses the relevant built-in test, program, e.g. IOP test. At 201 a delay time starts to enable the user to put on the blocking enclosure. At 202, the optimal exposure and focus are determined and locked by automatic algorithm that runs on the light source and the image capturing unit. At 203, the user's eyes are exposed to darkness for a first time period. In this manner, each pupil dilates to a respective first size, possibly maximal size. At 206, both eyes are illuminated by visible light for a second time period. At the end of the second time period, each pupil constricts to a respective second size. At 207, the eyes are exposed to darkness again for a third time period, and each pupil dilates to a respective third size at the end of the third time period. At 209, the eyes are illuminated once again by visible light for a fourth period of time.

At 210, images of light reflected from both eyes are captured at several time points starting when the light source is on. The plurality of images can be processed in order to determine each pupil size at each one of the different time points, and a graph like the one of FIG. 3 can be created for each pupil, showing variation of pupil size over time.

Optionally, at least within the first time period, soothing sounds are played at 204 in order to soothe the person, as explained above. The soothing sounds may be played throughout the test, until or beyond the illumination at 209. In some embodiments of the present invention, before the light is turned on at 206, the person may be informed that the light is about to be turned on and asked to keep the eyes open, at 205. In some embodiments of the present invention, before the light is turned on at 209, the person may be informed that the light is about to be turned on and asked to keep the eyes open, at 208.

Figure 4B:
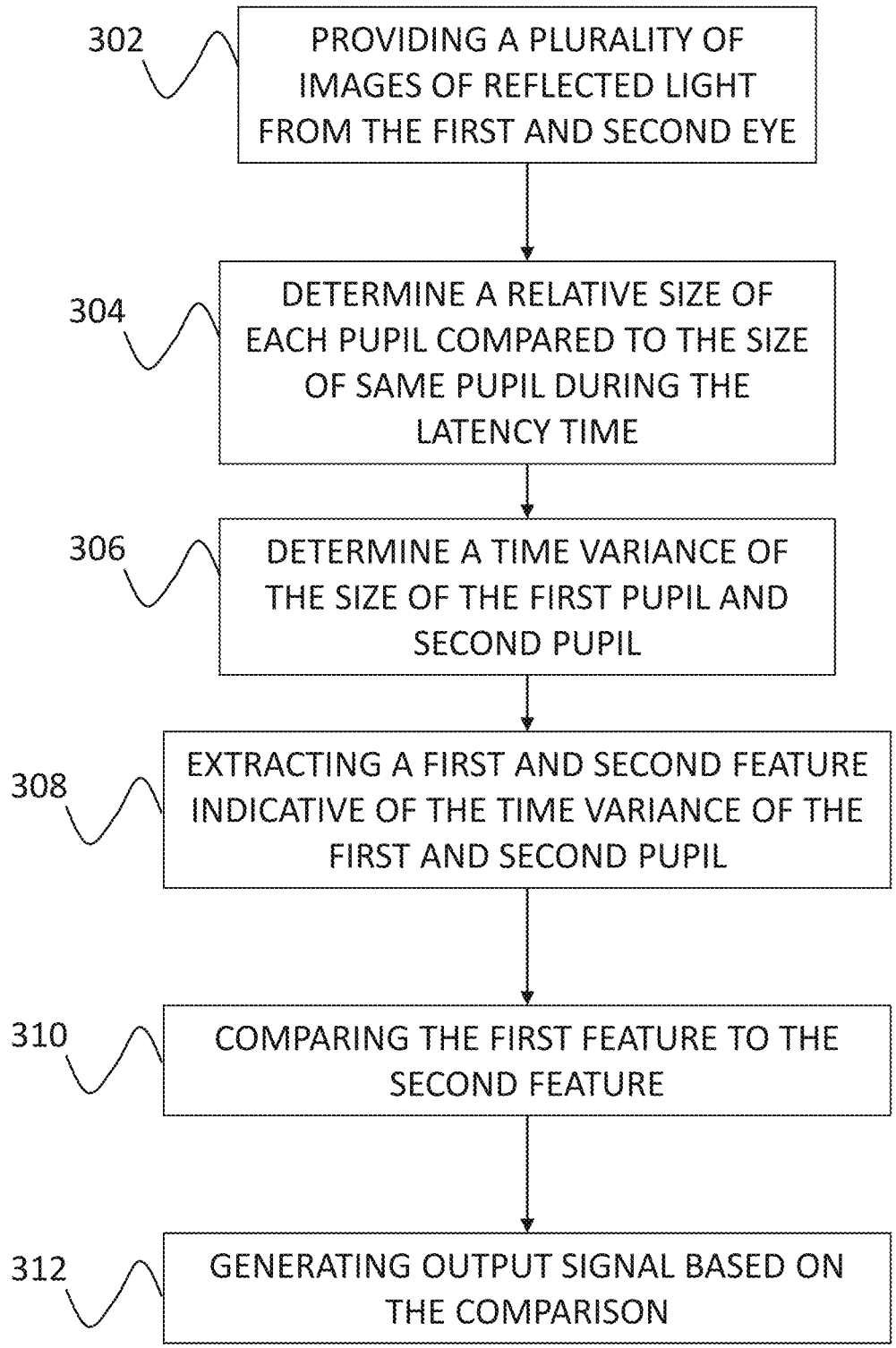

Reference is now made to FIG. 4b, which is a flowchart 300 illustrating a non-limiting exemplary method for processing images of a person's eyes in order to determine a condition of IOP of person's eyes. It is noted that the method 300 may be executed by using the system 100 and/or other processing utility (software or hardware or both).

At 302, a plurality of images is provided. The images are of light reflected from a person's eyes, when a visible light source is turned on and off at a certain schedule. The schedule may be any schedule of choice, and may, for example, be the schedule of the method of FIG. 4a. In some embodiments of the present invention, as explained above, the light reflected from the person's eyes is the same visible light illuminating the eye(s) and causing pupil constriction.

At 304, each image is processed, and the relative size of each pupil to its size during the latency period is determined for each image. The size of a pupil may be determined by measuring a diameter of the pupil, or by measuring an area of the pupil. In some embodiments of the present invention the area of the pupil is estimated by counting the number of pixels defining the image of the pupil.

At 306, based on the relative sizes of the pupils found at 304, a first graph is plotted for the first pupil and a second graph is plotted for the second pupil, showing a time variance (constriction speed) of the first and second pupils, respectively. The graphs, as mentioned, can be in the format shown in FIG. 3. At 308, at least one feature is extracted from the first graph and at least one corresponding feature is extracted from the second graph. For example, if the graphs for the pupils are similar to the graph of FIG. 3, the feature may be a function of any, some, or all of the quantities $S_1$, $S_2$, $S_3$, $\Delta t_2$, $\Delta t_3$ described in FIG. 3 and relating to a first pupil. Similarly, the corresponding feature of the second pupil may be a function of any, some, or all of the corresponding quantities $S'_1$, $S'_2$, $S'_3$, $\Delta t_2$, $\Delta t_3$ relating to the second pupil, (where the not-shown $S'_1$, $S'_2$, $S'_3$ correspond to $S_1$, $S_2$, $S_3$). The first feature F and the corresponding second feature F' may include, for example any of the following couples (each couple is listed in one raw below):

$$F = \frac{S_3}{S_1}; F' = \frac{S'_3}{S'_1}$$

$$F = \frac{S_3 - S_2}{S_1}; F' = \frac{S'_3 - S'_2}{S'_1}$$

$$F = \frac{S_3 - S_2}{S_1 - S_2}; F' = \frac{S'_3 - S'_2}{S'_1 - S'_2}$$

$$F = \frac{S_1 - S_2}{\Delta t_2}; F' = \frac{S'_1 - S'_2}{\Delta t_2}$$

$$F = \frac{S_3 - S_2}{\Delta t_3}; F' = \frac{S'_3 - S'_2}{\Delta t_3}$$

At 310, the feature F of the first pupil and the feature F' of the second pupil are compared to each other. The comparison may be, for example a difference between F and F', or a ratio of F and F'. In some embodiments of the present invention, the result of the comparison (e.g., the difference or ratio) is compared to a predetermined threshold. As mentioned above, the comparison between F and F' may be performed over several tests performed over several days. So, rather than comparing the feature F to the feature F', the sum or average value of F over several tests may be compared to the sum or average value of F' over the same several tests.

At 312, an output signal indicative of the result of the comparison is generated. In general, if F and F' are very different, the output signal causes an output unit to warn the user of this fact and to advise the user to perform medical checkups for elevated IOP. If, on the contrary, F and F' are within a certain range with respect to each other, the output signal causes the output unit to inform the user of this fact and advise that there is no need for further medical checkups regarding elevated IOP.

Figure 4C:
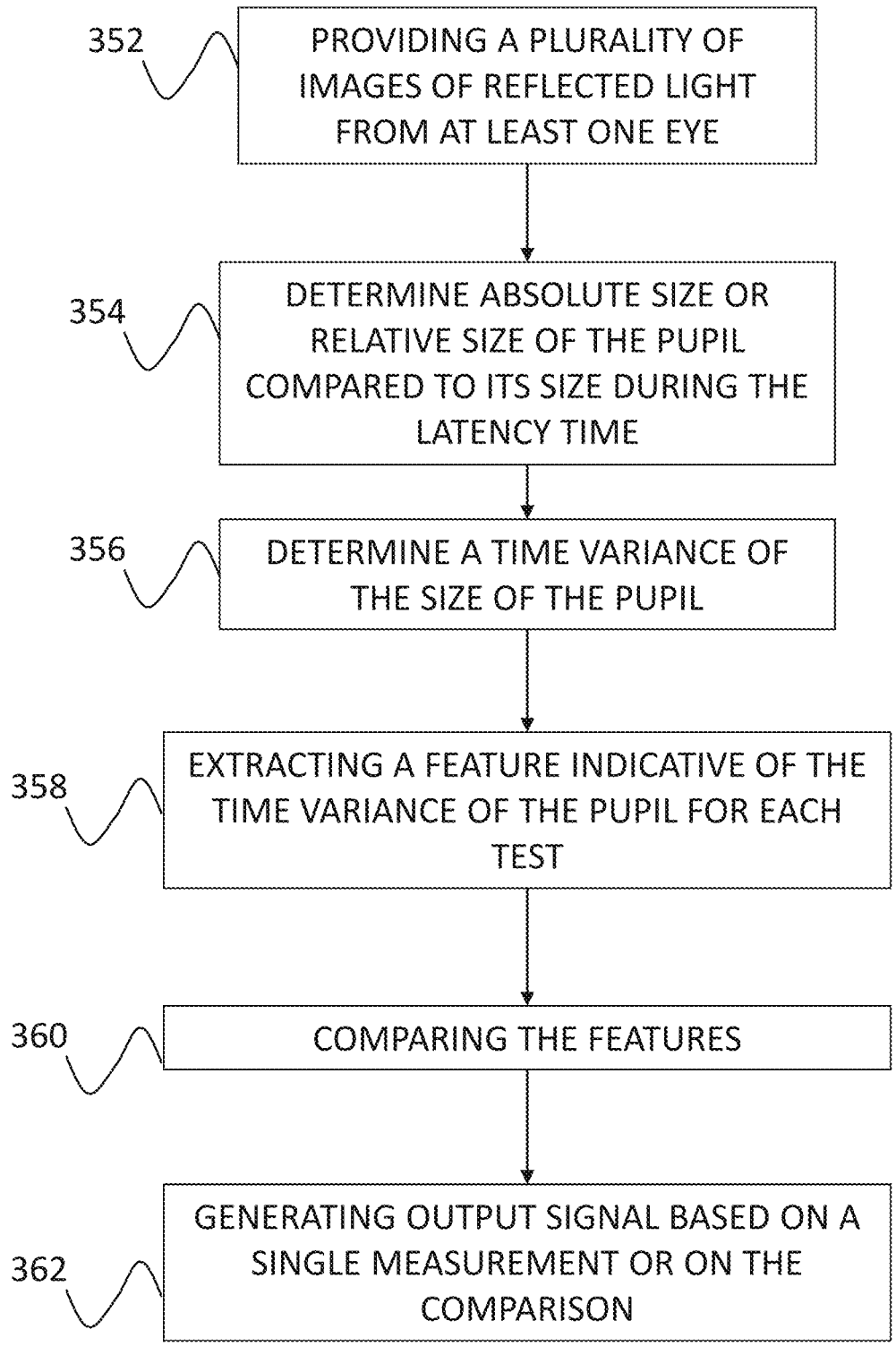

In some embodiments of the invention, the measurement schedule described in FIG. 4a can be performed on a single eye of a person for one or more times over the day, and the analysis of the images, obtained in each one of the measurements over the day, is carried out according to flowchart 350 in order to determine a condition (e.g. value) of IOP of person's eye as illustrated in FIG. 4c. It is noted that the method 350 may be executed by using the system 100 and/or other processing utility (software or hardware or both).

At 352, a plurality of images is provided. The images are of light reflected from a person's eye, when a visible light source is turned on and off at a certain schedule. The schedule may be any schedule of choice, and may, for example, be the schedule of the method of FIG. 4a. In some embodiments of the present invention, as explained above, the light reflected from the person's eye is the same visible light illuminating the eye(s) and causing pupil constriction.

At 354, each image is processed, and the absolute size of the pupil or the pupil's size relative to its size during the latency period is determined for each image. The size of a pupil may be determined by measuring a diameter of the pupil, or by measuring an area of the pupil. In some embodiments of the present invention the area of the pupil is estimated by counting the number of pixels defining the image of the pupil.

At 356, based on the relative sizes of the pupil found at 354, a graph is plotted for the pupil size, showing a time variance (constriction speed) of the pupil. The graph, as mentioned, can be in the format shown in FIG. 3.

At 358, at least one feature is extracted from each graph corresponding to one measurement/test. For example, if the graph for the pupil is similar to the graph of FIG. 3, the feature may be a function of any, some, or all of the quantities $S_1$, $S_2$, $S_3$, $\Delta t_2$, $\Delta t_3$ described in FIG. 3. The feature F may, for example, be any of the following:

$$F = \frac{S_3}{S_1}; F = \frac{S_3 - S_2}{S_1}; F = \frac{S_3 - S_2}{S_1 - S_2}; F = \frac{S_1 - S_2}{\Delta t_2}; F = \frac{S_3 - S_2}{\Delta t_3}$$

The same feature F is calculated for each measurement/test carried, such that at the end a plurality of features F1-Fn, corresponding to n measurements performed at different times of the day, are obtained.

At 360, the features F1-Fn of the pupil may be compared to each other. The comparison may be, for example a difference or a ratio between the features.

At 362, an output signal based on a single measurement or on the result of the comparison is generated.

In some embodiments, at least some of the features F1-Fn, or a relation between several features, can be used to obtain absolute value of the IOP in the tested eye. A calibration function correlating between the size of the pupil or the feature F and the actual, absolute, value of the IOP can be generated according to the invention.

In some embodiments, additional features can be obtained/calculated from image data collected by an infrared image capturing unit operated at least during the period ($\Delta t_3$), as described above.

In some embodiments, the test is carried out according to schedule illustrated in FIG. 3 with the time values of $\Delta t_2 = 1$ sec and $\Delta t_3 = 6$ sec. As it has been for example shown, that for short wavelength light (e.g. blue light) and the abovementioned time values, the least intra- and inter-individual coefficients of variation (cv<0.2) are obtained. This means that the differences between people having the same IOP with respect to the feature F, such as the feature $F = S_3/S_1$, are small. Therefore, by utilizing the method of the invention, it is possible to measure IOP for one person by comparing the feature F to a database of measurements relating to other people. In other words, for two people having the same IOP, the calibrated feature $F = S_3/S_1$ will be equal. By building a database that correlates between values of the feature F and the actual IOP, as measured for example by classic methods (e.g. a Goldman tonometer), for a large number of people, it will be possible to identify IOP for a new person by only measuring the feature F for him. Furthermore, this enables monitoring the IOP value of the same person by performing a plurality of tests and comparing between the features F obtained from the different tests.

Figure 5A:
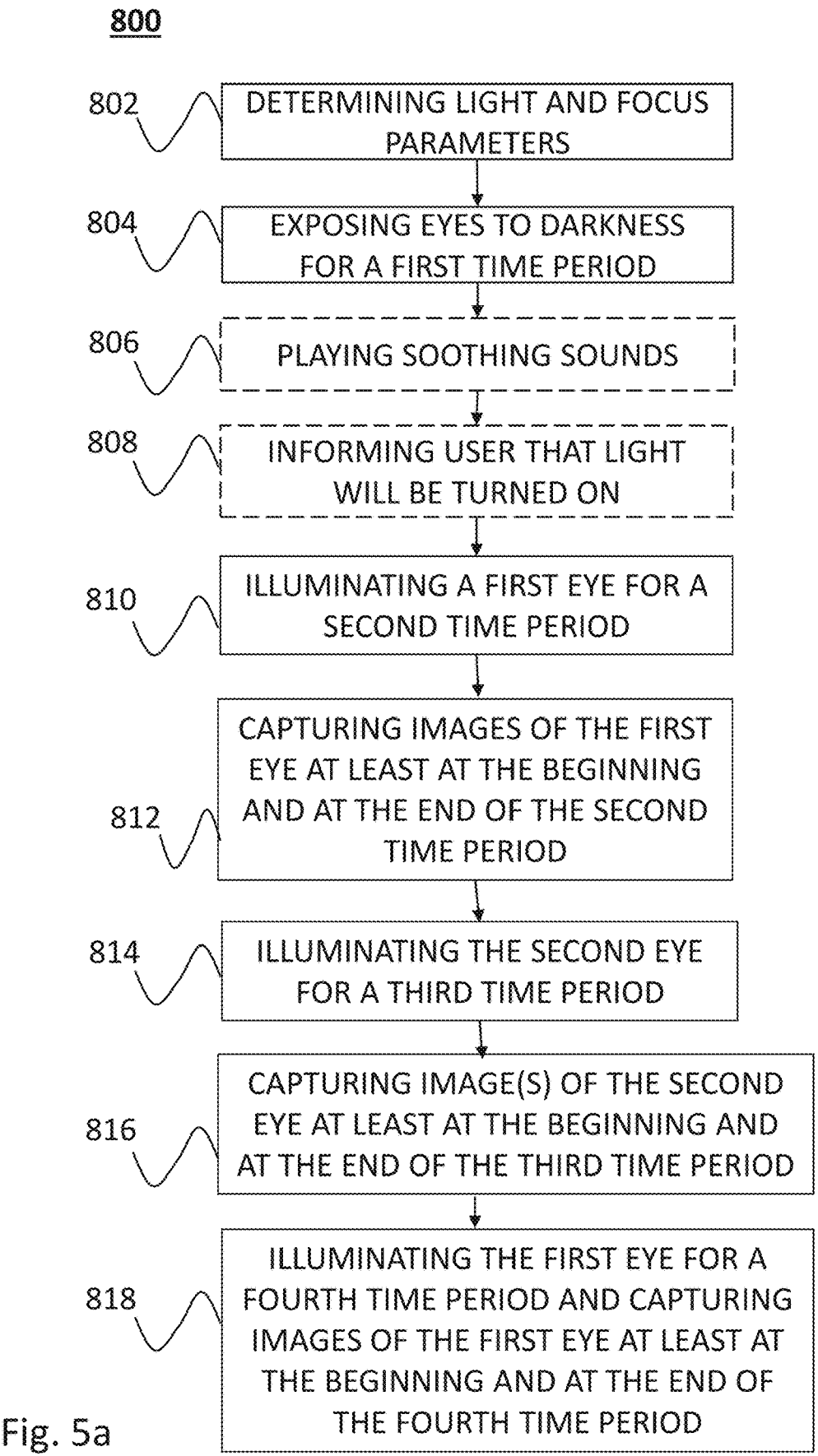
FIGS. 5a-5b illustrate another non-limiting example of a method for collecting and processing images of a person's pupils in order to determine a condition of the person's eyes.

Reference is now made to FIG. 5a, which is a flowchart 800 illustrating a non-limiting exemplary method for collecting images of a person's eyes in order to determine a condition of the person's eyes. It is noted that the method 800 may be executed by using the system 100 and/or other processing utility (software or hardware or both).

The method 800 can be executed to identify a condition of relative afferent pupillary defect (RAPD) affecting one or both eyes of the person. Generally, the so called swinging flashlight test is performed in order to diagnose RAPD.

At step 802, before the user puts on the light blocking enclosure, he/she types in the RAPD setup parameters and runs the test procedure. After a predetermined delay time, the optimal exposure and focus are determined and locked by automatic algorithm that runs on the light source and the image capturing unit.

At 804, in response to the user's input, the person's eyes are exposed to darkness for a first time period, e.g. for 30 seconds or so. In this manner, each pupil dilates to a respective first size, possibly maximal size. Optionally, at 806 and 808, at least within the first time period, soothing sounds are played in order to soothe the person, as explained above. Alternatively, the soothing sounds may be played throughout the test. In some embodiments, before the light is turned on, the person may be informed that the light is about to be turned on and asked to keep the eyes open.

At 810, one of the eyes is illuminated by visible light for a second time period, generally for a few seconds, e.g. 3-4 seconds. Consequently, the system 100 is configured to enable illumination of one eye at a time. This can be achieved by providing two light sources or at least two groups of light sources (light emitting units) each dedicated to illuminate one eye only, or by providing an optical directing arrangement configured and operable to direct the light from a single or multiple light source(s) to one eye at a time. In any case, the system 100 should preferably include an isolating structure, such as the barrier (fixed or removable) as described above and illustrated in FIG. 8*f* below, that constantly separates between the two eyes of the user with respect to light exposure.

During the second time period, at 812, the illuminated eye is imaged by the image capturing unit. It is possible to capture images during the whole second time period, at a predetermined rate, e.g. every 0.1 seconds, or at least at two separate time periods at the beginning and at the end of the second time period. The purpose of the images is to determine, as will be further described below, the sizes of the first pupil at least at the beginning and at the end of the second time period.

At 814, the second eye is illuminated by visible light for a third time period, that lasts as the second time period, e.g. for 3-4 seconds.

Similarly to step 812, at 816, images of the second eye are captured at least at the beginning and at the end of the third time period.

At 818, the first eye is illuminated for a fourth time period and images of the first eye are captured at least at the beginning and at the end of the fourth time period.

Similarly and optionally, while not specifically shown in the figure, it is possible to repeat the steps 814 and 816 for the second eye for a fifth time period.

The period of illumination, e.g. 3-4 seconds, is chosen to be long enough causing an exposed pupil of a healthy eye to constrict fully or almost fully. In some embodiments, the illumination period can be adjusted to different ages, as younger people have faster constriction reaction than elderly people.

Figure 5B:
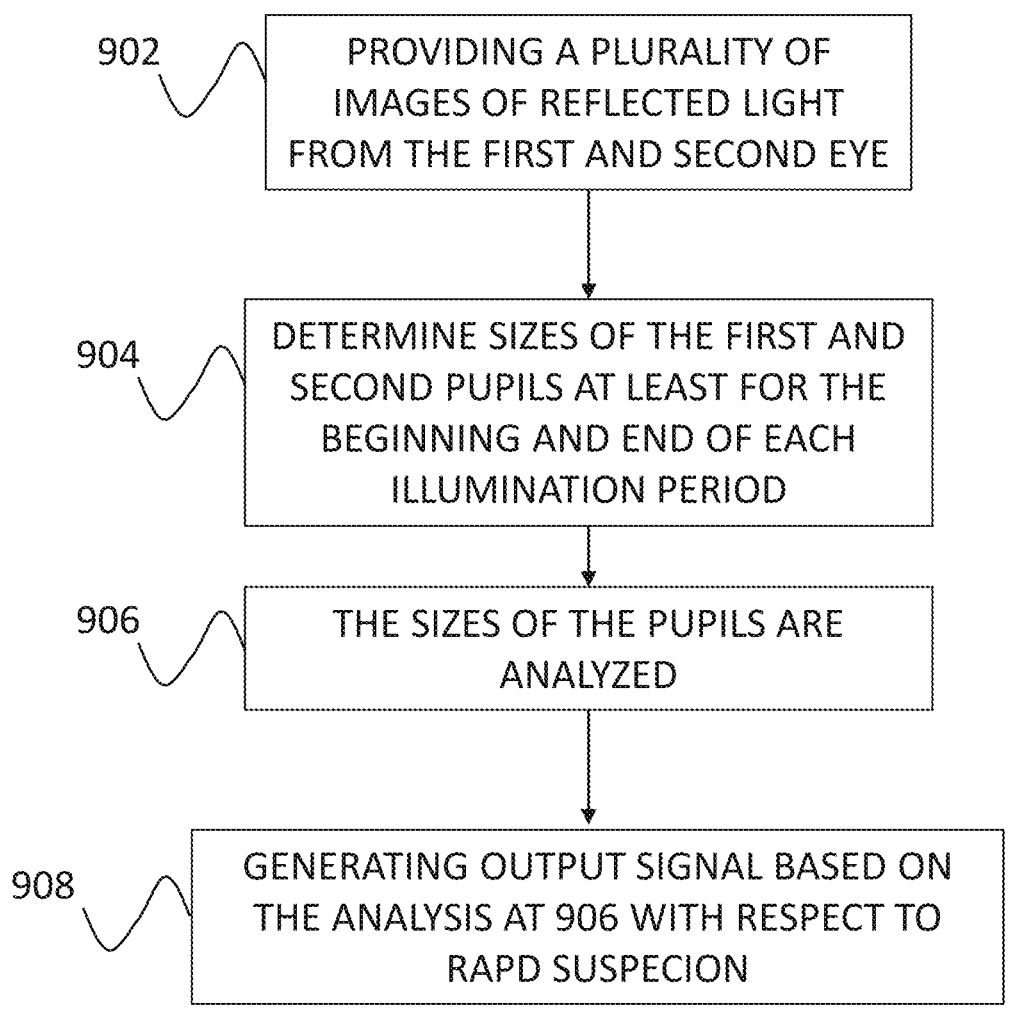

Reference is now made to FIG. 5*b* which is a flowchart 900 illustrating a non-limiting exemplary method for processing images acquired with method 800 of FIG. 5*a*. At 902, the images of both eyes are received, and at 904 the images are analyzed and the size of the respective pupil is determined for each image or for a group of consecutive images, such that the pupil size is an average or a median of the pupil sizes in the group of consecutive images. Consequently at least the following pupil sizes are determined:

1) $S1,1$ and $S1,2$ for the first pupil, corresponding to the beginning and the end of the second time period;
2) $S2,1$ and $S2,2$ for the second pupil, corresponding to the beginning and the end of the third time period;
3) $S1,3$ and $S1,4$ for the first pupil, corresponding to the beginning and the end of the second time period; and optionally
4) $S2,3$ and $S2,4$ for the second pupil, corresponding to the beginning and the end of the optional fifth time period.

At 906, the pupils sizes are analyzed and compared, and at 908 a corresponding output signal with respect to the risk of RAPD existence is generated.

It should be noted again that the images are obtained by capturing the visible light reflected from the eyes. Each eye is imaged while being illuminated. Utilizing the pupillary latency principle, the size of each pupil can be determined at the start of or immediately after the illumination has begun, because it takes time for the pupil to start constricting after being exposed to the visible light. Consequently, when swinging the light between the eyes, e.g. when moving from the first eye to the second eye, the size of the second eye when it has just been illuminated would be the same size of the second eye just before it was illuminated. This is used in the analysis of the pupils sizes in order to determine the risk of RAPD, while only using visible light cameras/image capturing units. The analysis of the pupils sizes depends on the consensual light reflex principle, i.e. that in normal situations the two pupils constrict equally when only one eye is exposed to light.

The analysis of the pupils sizes may be based on the following: In the literature, it is stated that during the swinging flashlight test, the first time the eyes are illuminated they will probably constrict. Therefore, in the analysis, the results of the first illumination (happening to the first eye during the second time period above) can be ignored. The rest of results can be analyzed as follows:

If $S2,2<S2,1$, then the second eye is healthy; this conclusion is enhanced if in addition $S2,2$ is very small;

If $S2,2 \geq S2,1$, then the second eye is not healthy;

If $S1,4 \leq S1,3$, then the first eye is healthy; it is noted that the first pupil may be closed or almost closed at the beginning of the third time period if the second eye is healthy (because of the consensual reflex principle), therefore if the first eye is also healthy we expect the first pupil to keep being closed.

If $S1,4>S1,3$, then the first eye is not healthy; because the pupil has enlarged;

If we add the optional step by illuminating the second eye during a fifth time period as described above; then the following analysis can be added:

If $S2,3>S2,2$; this enhances the conclusion that the first eye is not healthy;

If $S2,3<S2,2$; this enhances the conclusion that the first eye is healthy;

If $S2,4 \geq S2,3$; this enhances the conclusion that the second eye is not healthy; and If $S2,4 \leq S2,3$; this enhances the conclusion that the second eye is healthy.

It is possible to repeat the test by starting illuminating the second eye firstly, then comparing the results.

Figure 6:
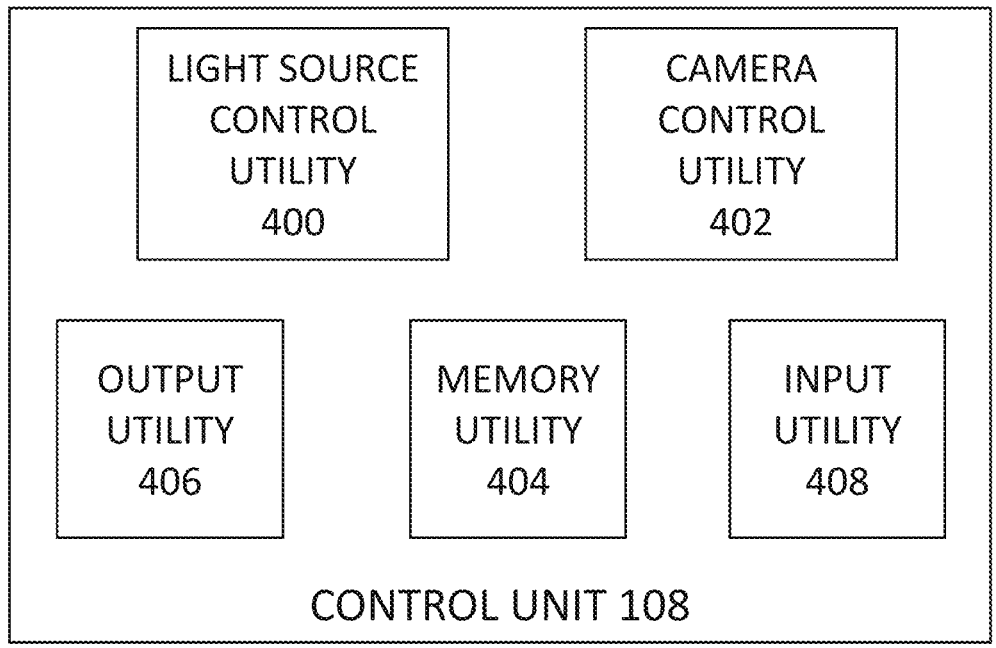
FIG. 6 illustrates in a block diagram a non-limiting example of one component of the system of the present invention.

FIG. 6 is a block diagram illustrating a non-limiting example of the control unit 108 configured for being used as part of a binocular pupillary response monitoring apparatus, according to some embodiments of the present invention. The control unit 108 includes a light source control utility 400, a camera control utility 402, a memory utility 404, and may include an output utility 406 and an input utility 408. The term "utility" herein refers to a unit including software and/or hardware modules configured for performing one or more particular functions.

The light source control utility 400 is configured for controlling an operation of a light source, by turning the light source on and off according to one or more schedules. The camera control utility 402 is configured for controlling an operation of an image capturing unit, in order to cause the image capturing unit to capture images of light reflected from the eyes at a desired rate and according to a desired schedule, which corresponds to the time intervals in which the light source is on. The camera control utility 402 may be further configured for controlling the focal length of the image capturing unit, in order to ensure that the captured images of user's eyes are properly focused.

The memory utility 404 is configured for storing first instructions indicative of a schedule to be used by the light source control utility 400 for turning the light source on and off. Optionally, the memory utility 404 is configured for storing a plurality of sets of first instructions, each set of first instructions being indicative of a different schedule. The desired set of first instructions may be visualized via the output utility 406 and selected via the input utility 408, or via the input/output interface of FIGS. 2a and 2b.

In some embodiments of the present invention, the memory utility 404 is further configured for storing second instructions to be used by the camera control unit 402 for controlling the operation of the image capturing unit. Optionally, the memory utility 404 is configured for storing a plurality of sets of second instructions, each set of second instructions being indicative of a different schedule. The desired set of second instructions may be visualized via the output utility 406 and selected via the input utility 408, or via the input/output interface of FIGS. 2a and 2b.

According to some embodiments of the present invention, the memory utility 404 stores user profile data for one or more users, as described above. In some embodiments of the present invention, the user profile data includes a history of the user's tests. For example, the values of the features F and F' taken on different days and/or at different times may be stored for later processing, each value having a time stamp indicating when the value was measured/calculated.

The input utility 408 is configured for receiving an input from a user to start the schedule of the light source and/or image capturing unit, and for instructing the light source control utility 400 and the camera control utility 402 to operate the light source and the image capturing unit according to the respective schedules. In one specific non-limiting example, the light source and/or the image capturing unit can be controlled via wired or wireless communication such as Bluetooth. For example, this is the case when the light source is located in the blocking enclosure and the user uses a smartphone to control the light source remotely.

The output utility 406 is configured for controlling the operation of the output interface, according to a schedule thereof. For example, as mentioned above, the output interface may play soothing music and play a message to the user to keep the eyes open. The memory utility 404 may further store data (graphical data, audio data, haptic data, etc.) configured for being output by the output utility and may store instructions indicative of a schedule of the output.

Figure 7:
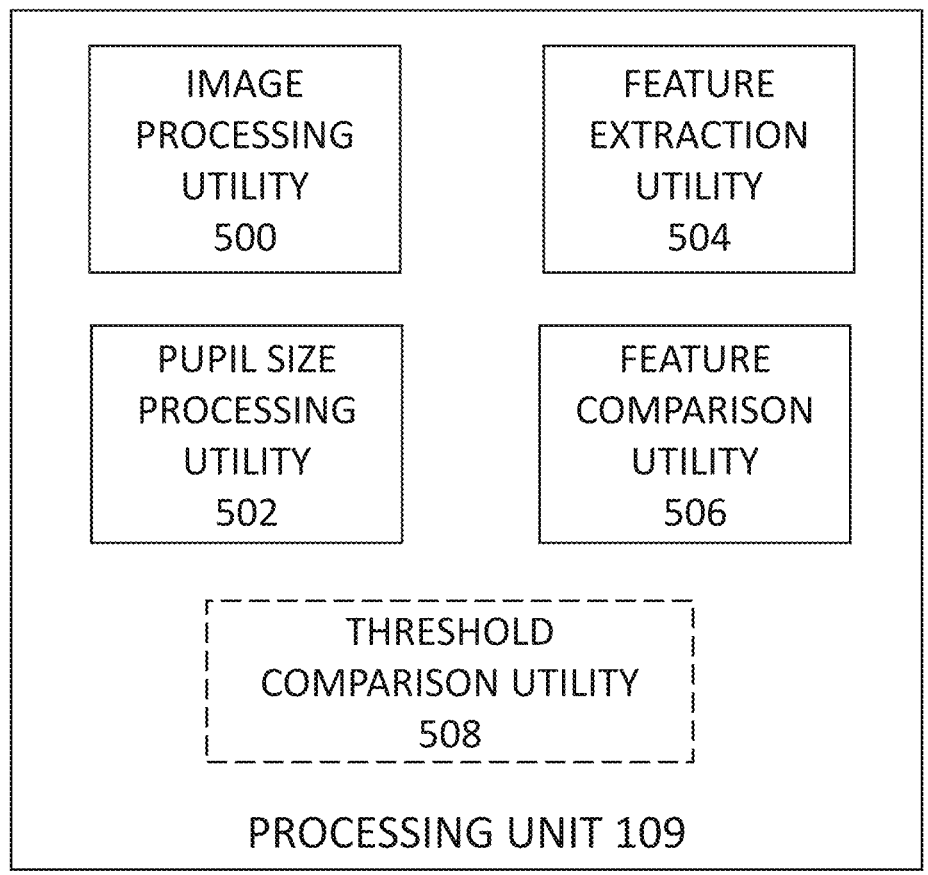
FIG. 7 illustrates in a block diagram a non-limiting example of a second component of the system of the present invention.

FIG. 7 is a block diagram illustrating a non-limiting example of the processing unit 109 configured for being used with a binocular pupillary response monitoring apparatus, according to some embodiments of the present invention. Specifically, FIG. 7 exemplifies in some aspects the IOP test. However, those skilled in the art would appreciate that similar application with suitable modifications and utilities can be adjusted for the RAPD test. As described above, the processing unit 109 may be an integral part of the binocular pupillary response monitoring apparatus, or may be located externally to the binocular pupillary response monitoring apparatus and communicating therewith via a wired or wireless network.

The processing unit 109 includes an image processing utility 500, pupil size processing utility 502, a feature extraction utility 504, a feature comparison utility 506, and optionally a threshold comparison utility 508.

The image processing utility 500 is configured for receiving image data from an image capturing unit (as described in FIGS. 2a-2b), and for determining a size of the pupils in each image. The pupil size processing utility 502 is configured for using the pupil sizes determined by the image processing utility 500 to yield data indicative of a time variance of the size of each pupil. The feature extraction utility 504 is configured for extracting at least one feature of the time variance of the size of each pupil, as described above. The feature comparison utility 506 is configured for comparing a feature of the first pupil with a corresponding feature of the second pupil, or for comparing the sizes of the pupils, as described above, and for generating an output signal indicative of the result of the comparison, as explained above. Optionally, the feature comparison utility is configured for transmitting a result of the comparison to the threshold comparison utility 508. The threshold comparison utility 508 is configured for comparing the result of the comparison to a threshold, and for generating an output signal indicative of the result of the comparison with the threshold, as explained above.

Figure 8A:
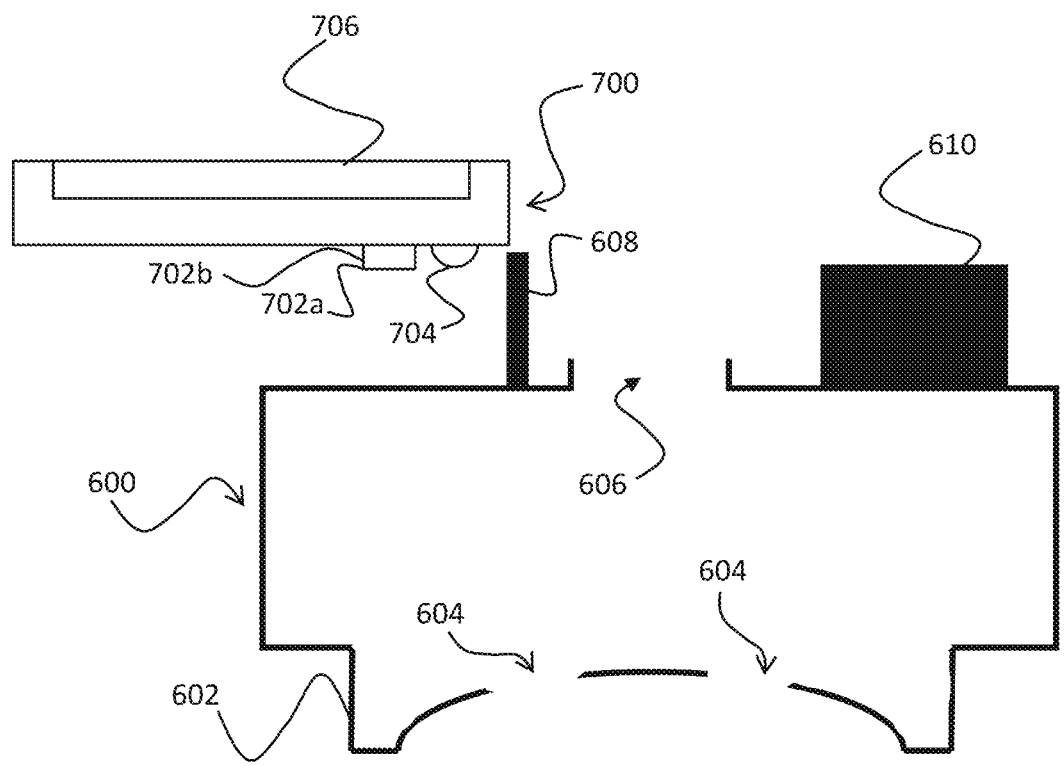
Figure 8B:
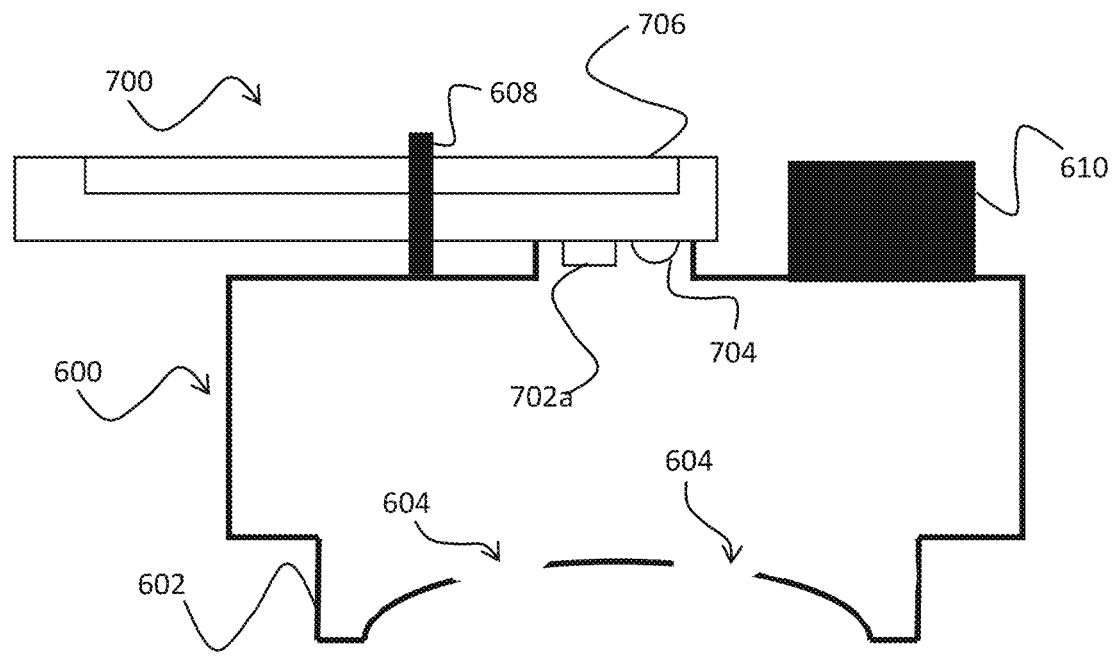
Figure 8D:
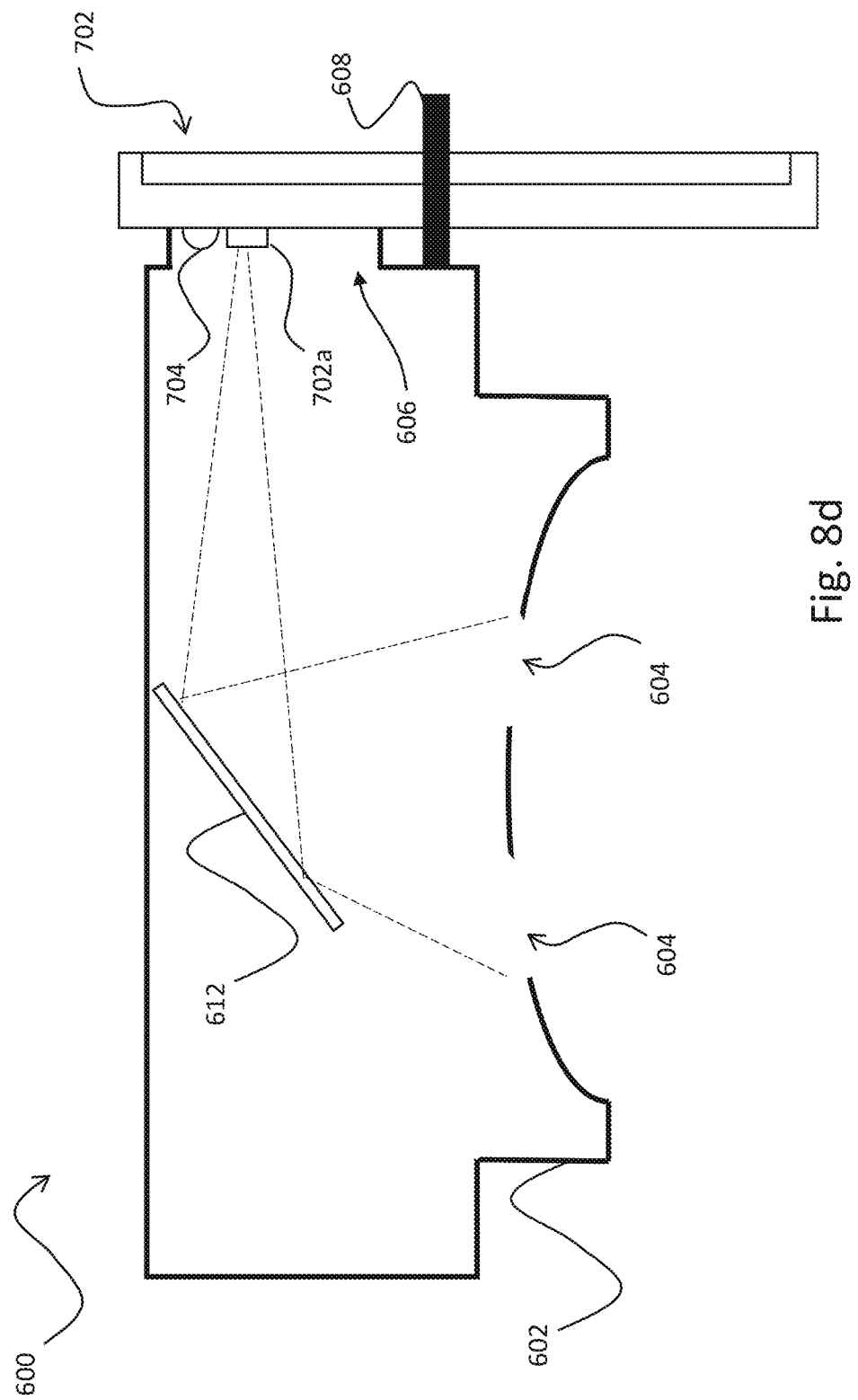
Figure 8E:
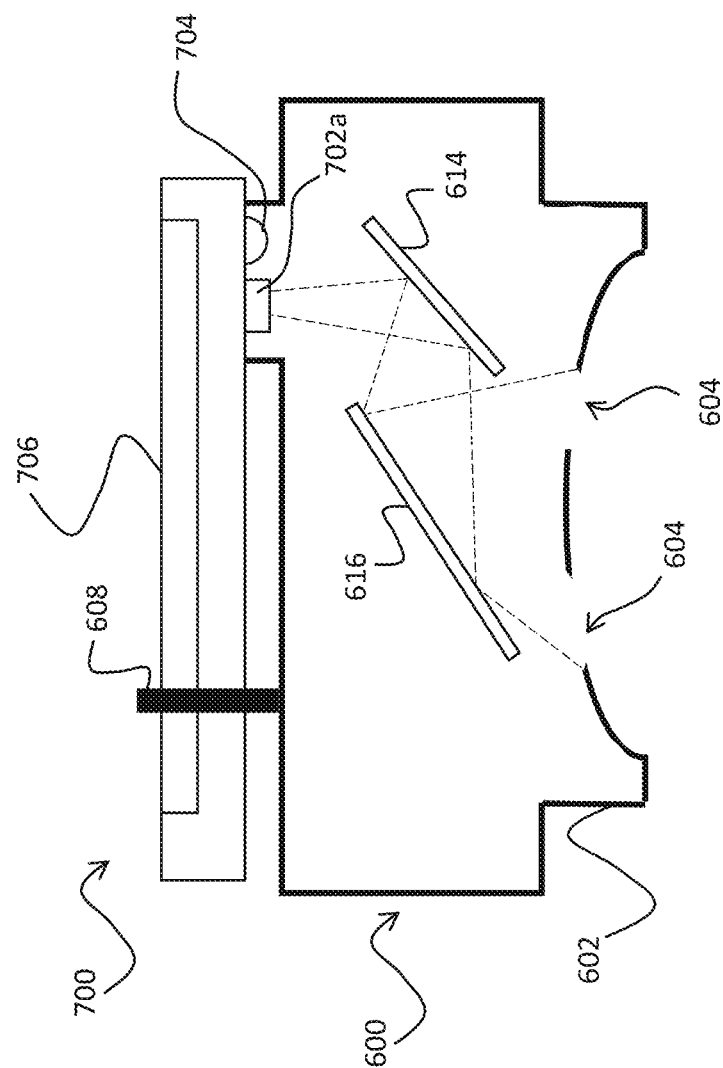

FIGS. 8a-8f are schematic diagrams illustrating non-limiting examples of a light blocking enclosure of the present invention, for being used in conjunction with a smartphone or tablet computer in order to assess a condition of the eyes of a user. FIG. 8a exemplifies the enclosure 600 from a top view. FIG. 8b exemplifies the enclosure 600 from a top view, when joined to a smartphone or tablet 700. FIG. 8c exemplifies the enclosure 600 from a side view, when joined to a smartphone or tablet 700. FIG. 8d exemplifies the enclosure 600 from a top view, when joined to a smartphone or tablet 700, the enclosure including at least one optical arrangement 612 configured for directing light reflected from the eyes to the aperture of the smartphone's camera. FIG. 8e exemplifies the enclosure 600 from a top view, when joined to a smartphone or tablet 700, the enclosure including a periscope optical arrangement 614 and 616 configured for directing light reflected from the eyes to the aperture of the smartphone's camera. The periscope optical arrangement may be particularly useful whenever the smartphone's camera is not centralized with respect to the enclosure. It should be noted that the optical arrangement 612 and the periscope optical arrangement 614 and 616 can be used as needed with any light blocking enclosure of the invention, including, but not limited to, the light blocking enclosure 102 described with respect to system 100 of FIGS. 2a-2b. FIG. 8f exemplifies the enclosure 600 from a top view, the enclosure including a barrier 618 dividing the inside of the enclosure into two compartments each for receiving and illuminating only one of the two eyes. This configuration is especially useful when performing a RAPD test as described above.

The enclosure 600 includes an eyepiece 602 which includes one or two first openings 604 configured for receiving the eyes of a user 114. Optionally, the enclosure includes a holder 608 configured for holding a smartphone/tablet 700. The holder can be configured to accept a plurality of smartphones having different sizes, for example can be configured with a spring mechanism as shown. The enclosure 600 further includes a second opening 606 configured for being covered by the smartphone/tablet 700 when the smartphone/tablet 700 is held by the holder 608, such that a light source 704 of the smartphone/tablet and an aperture 702a of the smartphone/tablet's camera 702b are located at the second opening 606 and have a line of sight with the first opening(s) 604. It should be understood that in some embodiments, the light source is provided within the enclosure 600 and the flash in the smartphone is not used. In such case, the smartphone is used to capture images by its camera system 702b and optionally to control the light source included in the enclosure (e.g. via Bluetooth communication) and/or to process the image data with its processor. In some embodiments of the present invention, the enclosure 600 includes a counterweight 610 configured for countering a weight of the smartphone/tablet 700 and balancing the enclosure with respect to the two eyes of the user, so that the enclosure 600 does not tilt when the smartphone/tablet 700 is joined to the enclosure 600. Optionally, the positions of the smartphone/tablet 700 and the counterweight are adjustable to enable using different smartphones/tablets, as different smartphones/tablets may have different shapes and weights.

Optionally, different models of the enclosure 600 are configured for matching with respective smartphones/tablets. For this, the location of the second opening and the shape, weight, and location of the counterweight 610 are configured for matching the geometry of smartphone/tablet that the enclosure 600 is configured to be joined to.

In some embodiments of the present invention, as shown, for example, in FIGS. 8a and 8b, there is a direct line of sight between the light source 704 and the first opening(s) 604, and between the camera aperture 702 and the first opening(s) 604. In other embodiments of the present invention, the line of sight is not direct and an optical arrangement 612 is required for directing light from the light source towards the user eye(s) and/or directing reflected light from the eye(s) of the user to the camera aperture 702, as shown in FIGS. 8d and 8e. In FIG. 8d, the optical arrangement 612 may include one or more optical units (such as mirrors and/or lenses, for example) to control/change the direction of the axis of propagation of the light once. In FIG. 8e, the optical arrangement may include two mirrors 614 and 616 to change the direction of the axis of propagation of light twice. In general, any optical arrangement can be used to change the direction of the axis of propagation as many times as desired.

The smartphone/tablet 700 includes a camera 702b having an aperture 702a and a flash light source 700. The smartphone/tablet 700 also includes a control unit (not shown) configured and operable for controlling the camera and flash light source according to respective schedules, as explained above. The smartphone/tablet 700 may store, in a memory utility thereof, an application software including computer readable instructions configured for running on the smartphone's processor(s) causing the smartphone/tablet 700 to perform the methods of FIGS. 4a, 4b, 4c, 5a and/or 5b as performed by the control unit and the processing unit of FIGS. 2, 6, and 7. When the computer readable instructions run on the smartphone/tablet's processor(s), the screen 706 or buttons of the smartphone/tablet 700 may be used as a user input to instruct the smartphone/tablet to start performing the steps of the methods of FIGS. 4a, 4b, 4c, 5a and/or 5b.

In the example of FIG. 8f, the enclosure includes a barrier 618 configured for separating between the two eyes by dividing the inside of the enclosure into two compartments, such that each compartment includes a light source, 620a and 620b, each dedicated for illuminating one eye only. The enclosure may be configured for use with a smartphone/tablet, as shown, to use the camera system 702b for capturing images, or alternatively the enclosure may be fitted with an independent camera system (not shown). In either case, the camera would be positioned to have a line of sight with both eyes, e.g. such that the barrier is located at the central axis of the camera as shown in the figure. Alternatively, in some embodiments, the enclosure may be fitted with two cameras each located in one of the two compartments and each configured to be controlled to capture images of the eye received at the respective compartment.

Optionally, a speaker of the smartphone/tablet 700 may be used to emit soothing music and/or to ask the user to keep his/her eyes open. The smartphone/tablet 700 may include a processing unit configured for processing the images of the user's eyes, as described above, or may be in communication with a remote processing unit configured for processing the images of the user's eyes. The speaker, display 706, or haptic unit of the smartphone/tablet may be configured for informing the user about the results of the eyes' assessment and advise the user accordingly.

The light source 704 of the smartphone/tablet 700 is a source of visible light (e.g., the flash of the smartphone/tablet's camera), and the smartphone/tablet 700 stores a software application in the form of computer-readable instructions configured for causing the smartphone/tablet's processor to control the operation of the smartphone/tablet, according to the methods described in FIGS. 4a, 4b, 4c, 5a and 5b. The computer-readable instructions of the present invention may be in the form of an application executable by the smartphone/tablet 700. As a non-limiting example, the part of the application relating to the methods of FIGS. 4a and 4b are described in more detail below. When the application is started by the user, the application causes the smartphone/tablet 700 to wait for a user input. The user input may be received when the user interacts with one or more of the input units/interfaces of the smartphone/tablet 700. For example, the input may be received when the user touches the touchscreen 706 or presses a button of the smartphone/tablet 700.

After the user input is received by the smartphone/tablet, the smartphone calibrates the light intensity and the focus (step 200 of the method of FIG. 4a), and possibly informs the user that the measurement session can be started or will automatically start. Then, the smartphone/tablet keeps its light off for the first time period (step 201 of the method of FIG. 4a). A speaker of the smartphone/tablet 700 may play a soothing sound (as per step 202 of the method of FIG. 4a), and an output may be produced by an output unit of the smartphone/tablet 700 (e.g. a speaker or a haptic device) to inform the user that the light of the smartphone/tablet 700 is about to be turned on and/or tell the user to keep his eyes open (as per step 203 of the method of FIG. 4a). The light of the smartphone/tablet 700 is turned on for a second time period (as per step 204 of the method of FIG. 4a). The light of the smartphone/tablet is then turned off for a third time period (as per step 206 of the method of FIG. 4a). An output may be produced by an output unit of the smartphone/tablet 700 (e.g. a speaker or a haptic device) to inform the user that the light of the smartphone/tablet 700 is about to be turned on and/or tell the user to keep his eyes open (as per step 207 of the method of FIG. 4*a*). The light of the smartphone/tablet is turned on for a fourth time period (as per step 208 of the method of FIG. 4*a*). The camera of the smartphone tablet captures images of visible and/or IR light reflected from the eyes (as per step 210 of the method of FIG. 4*a*).

When the test/measurement session described by FIG. 4*a* is concluded, or when several tests/measurement sessions as described by FIG. 4*a* are performed over several times/days, the application is configured for causing processing of the images captured by the camera of the smartphone/tablet, according to the method of FIG. 4*b* or 4*c*. The processing may be processed directly by the processor of the smartphone/tablet, or may be transmitted via a communication unit of the smartphone/tablet to a remote server/processor to be processed there.

Similar computer-readable instructions are included in the application which when run on the smartphone/tablet's processor cause the processor to perform the steps of the methods 5*a* and 5*b*.

Therefore, the present invention provides novel systems configured and operable to aid in monitoring one or more conditions of individual's eye(s). The novel systems are configured and operable to execute novel methods for monitoring eye(s) condition(s). Examples of such conditions include difference in intra ocular pressure (IOP) and risk of relative afferent pupillary defect (RAPD).

The invention claimed is:

1. A pupillary response monitoring system comprising:
   (a) a light-blocking enclosure with an open end for receiving a first eye and a second eye of an individual;
   (b) a light source, configured and operable for emitting visible light inside the enclosure and illuminating at least one eye of said first eye and second eye, according to a predetermined illumination schedule;
   (c) an image capturing unit, configured and operable for receiving visible light reflected from the first eye and/or the second eye, while each eye being illuminated by said light source, and for capturing a plurality of images, at a specific rate, of the first eye and/or the second eye;
   (d) a control unit configured and operable for:
      controlling an operation and the illumination schedule of the light source and defining a required exposure to illuminate the first and second eyes simultaneously;
      controlling an operation of the image capturing unit to determine and lock focus thereof and to capture the plurality of images of the first and second eyes simultaneously; and
      receiving from the image capturing unit first data indicative of the plurality of images;
   (e) a processing unit configured and operable for:
      processing the first data to determine second data indicative of a size of a pupil of the first eye and/or a size of a pupil of the second eye in each of said plurality of images;
      processing the second data by extracting from the second data at least one feature indicative of a variance of the size of the pupil of the first eye and the size of the pupil of the second eye, to thereby enable determining an ophthalmological condition indicative of intra ocular pressure (TOP) condition of the individual using the system in accordance with variance of the size of the pupil at different time points; and
      generating an output signal indicative of said ophthalmological condition; and
   (f) an output interface, configured for receiving the output signal from the processing unit and presenting the output to the individual;
   wherein said control unit is configured and operable to control said predetermined illumination schedule comprising: (i) a first illumination step comprising exposing the first and second eyes to darkness for a first time period; (ii) a second illumination step comprising illuminating the first and second eyes for a second time period and capturing images of the first and second eyes simultaneously; (iii) a third illumination step comprising exposing the first and second eyes to darkness for a third time period shorter than the first time period; (iv) a fourth illumination step comprising illuminating the first and second eyes for a fourth time period and capturing images of the first and second eyes simultaneously.

2. The system according to claim 1, wherein said control unit is configured and operable to control the image capturing unit to capture the plurality of images at the specific rate such that at least one image is captured for the illuminated at least one eye during 0.3 seconds of onset of the illumination schedule.

3. The system according to claim 1, further comprising a mobile device, wherein said mobile device comprises said image capturing unit, said control unit and said output interface.

4. The system according to claim 3, wherein said mobile device further comprises said light source.

5. A pupillary response monitoring system comprising:
   (a) a light-blocking enclosure with an open end for receiving a first eye and a second eye of an individual;
   (b) a light source, configured and operable for emitting visible light inside the enclosure and illuminating at least one eye of said first eye and second eye, according to a predetermined illumination schedule;
   (c) an image capturing unit, configured and operable for receiving visible light reflected from the first eye and/or the second eye, while each eye being illuminated by said light source, and for capturing a plurality of images, at a specific rate, of the first eye and/or the second eye;
   (d) a control unit configured and operable for:
      controlling an operation and the illumination schedule of the light source and defining a required exposure and illuminate one eye;
      controlling an operation of the image capturing unit to determine and lock focus thereof and to capture the plurality of images of; and
   receiving from the image capturing unit first data indicative of the plurality of images;
   (e) a processing unit configured and operable for:
      processing the first data to determine second data indicative of a size of a pupil of the first eye and/or a size of a pupil of the second eye in each of said plurality of images of said one eye;
      processing the second data by extracting from the second data at least one feature indicative of a variance of the size of the pupil of said one eye, to enable determining an ophthalmological condition indicative of intra ocular pressure (IOP) condition of the individual using the system; and
      generating an output signal indicative of said ophthalmological condition; and if) an output interface, configured for receiving the output signal from the processing unit and presenting the output to the individual, wherein said control unit is configured and operable to control said predetermined illumination schedule comprising: (i) a first illumination step comprising exposing the eye to darkness for a first time period; (ii) a second illumination step comprising illuminating the eye for a second time period and capturing images of the eye; (iii) a third illumination step comprising exposing the eye to darkness for a third time period shorter than the first time period; (iv) a fourth illumination step comprising illuminating the eye for a fourth time period and capturing images of the eye.

6. The system according to claim 5, wherein said processing unit is configured and operable to generate said value of TOP by comparing said at least one feature indicative of a variance of the size of the pupil of the eye to a database.

7. The system according to claim 5, further comprising an infra-red source and an infra-red sensor, configured and operable to be activated at least during the third illumination step to respectively illuminate the eye with infra-red light and capture infra-red images of the eye, said processing unit being configured and operable to analyze said infra-red images to determine said ophthalmological condition being a value of intra ocular pressure (IOP) in said eye.

8. A method for monitoring pupillary response, the method comprising illuminating at least one eye of first and second eyes of an individual with visible light according to a predetermined illumination schedule, and capturing a plurality of images, at a specific rate, of said at least one eye by detecting reflected light of said visible light, and processing said images to determine for each image a pupil parameter indicative of a size of a pupil of said at least one eye, and analyzing said pupil parameter in the plurality of images to thereby determine an ophthalmological condition indicative of intra ocular pressure (IOP) condition of the individual; wherein said predetermined illumination schedule comprises: (i) a first illumination step comprising exposing one of the first and second eyes to darkness for a first time period; (ii) a second illumination step comprising illuminating the same eye for a second time period and capturing images of the eye; (iii) a third illumination step comprising exposing the eye to darkness for a third time period shorter than the first time period; (iv) a fourth illumination step comprising illuminating the eye for a fourth time period and capturing images of the eye.

9. The method according to claim 8, wherein said ophthalmological condition is a value of intra ocular pressure (IOP) in the eye, wherein said value of IOP is generated by analyzing said pupil parameter and determining at least one feature indicative of a variance of the size of the pupil of the eye and comparing said feature to a database.

10. The method according to claim 9, further comprising illuminating eye with infra-red light and capturing infra-red images of the eye during said third illumination step and analyzing said infra-red images for determining said ophthalmological condition being a value of intra ocular pressure (IOP) in said eye.

11. The method according to claim 9, further comprising using a processing unit for processing said images of the eye and comparing sizes of pupil of said at least one eye at different time points during a measurement session.

12. A method for monitoring pupillary response, the method comprising illuminating simultaneously of first and second eyes of an individual with visible light according to a predetermined illumination schedule, and capturing a plurality of images, at a specific rate, of said at least one eye by detecting reflected light of said visible light, and processing said images to determine for each image a pupil parameter indicative of a size of a pupil of said at least one eye, and analyzing said pupil parameter in the plurality of images to thereby determine an ophthalmological condition indicative of intra ocular pressure (IOP) condition of the individual, wherein said predetermined illumination schedule comprises: (i) a first illumination step comprising exposing the first and second eyes to darkness for a first time period; (ii) a second illumination step comprising illuminating the first and second eyes for a second time period and capturing images of the first and second eyes simultaneously; (iii) a third illumination step comprising exposing the first and second eyes to darkness for a third time period shorter than the first time period; (iv) a fourth illumination step comprising illuminating the first and second eyes for a fourth time period and capturing images of the first and second eyes simultaneously.

13. A non-transitory computer readable medium including one or more sequences of instructions for monitoring pupillary response of an individual, wherein execution of the one or more sequences of instructions by one or more processors of a computing device comprising a camera causes the computing device to perform a process comprising:
  activating and controlling a light source to illuminate at least one eye of first and second eye(s) of the individual according to a predetermined illumination schedule;
  acquiring a plurality of images of said at least one eye by said camera, while being illuminated by said light source, according to a specific rate;
  processing said plurality of images to thereby determine quantitative data indicative of a size of a pupil of the at least one eye in each of said plurality of images; and
  analyzing said quantitative data and determining whether the quantitative data is indicative of one of the following ophthalmology conditions:
  difference in Intraocular Pressure (IOP) between the first and second eyes,
  Value of IOP in at least one of the first and second eyes; and
  generating corresponding output data to be presented to the individual;
  wherein said predetermined illumination schedule comprises: (i) a first illumination step comprising exposing one of the first and second eyes to darkness for a first time period; (ii) a second illumination step comprising illuminating the same eye for a second time period and capturing images of the eye; (iii) a third illumination step comprising exposing the eye to darkness for a third time period shorter than the first time period; (iv) a fourth illumination step comprising illuminating the eye for a fourth time period and capturing images of the eye.

14. The computer readable medium according to claim 13, wherein said one or more sequences of instructions comprise:
  controlling said light source to illuminate the first and second eyes simultaneously;
  acquiring said plurality of images of the first and second eyes simultaneously;
  processing said quantitative data by extracting from the quantitative data at least one feature indicative of a variance of the first pupil size and the second pupil size.

15. The computer readable medium according to claim 13, wherein said one or more sequences of instructions comprise:
- controlling said light source to illuminate one of the first and second eyes;
- acquiring said plurality of images of the eye while being illuminated;
- processing said quantitative data by extracting from the quantitative data at least one feature indicative of a variance of the pupil size, and performing a comparison of the at least one feature to a database; and
- generating said output signal indicative of value of IOP in the eye.

* * * * *